(12) United States Patent
Konstantino et al.

(10) Patent No.: US 11,420,030 B2
(45) Date of Patent: *Aug. 23, 2022

(54) METHODS AND SYSTEMS FOR DELIVERING SUBSTANCES INTO LUMINAL WALLS

(71) Applicant: ANGIOSCORE, INC., Colorado Springs, CO (US)

(72) Inventors: Eitan Konstantino, Orinda, CA (US); Michal Konstantino, Orinda, CA (US)

(73) Assignee: ANGIOSCORE, INC., Colorado Springs, CO (US)

(*) Notice: Subject to any disclaimer, the term of this patent is extended or adjusted under 35 U.S.C. 154(b) by 496 days.

This patent is subject to a terminal disclaimer.

(21) Appl. No.: 16/434,205

(22) Filed: Jun. 7, 2019

(65) Prior Publication Data
US 2019/0321603 A1    Oct. 24, 2019

Related U.S. Application Data

(60) Continuation of application No. 15/431,302, filed on Feb. 13, 2017, now Pat. No. 10,342,960, which is a
(Continued)

(51) Int. Cl.
*A61B 17/22* (2006.01)
*A61M 25/10* (2013.01)
(Continued)

(52) U.S. Cl.
CPC ..... *A61M 25/104* (2013.01); *A61B 17/22032* (2013.01); *A61B 17/320725* (2013.01);
(Continued)

(58) Field of Classification Search
CPC .............. A61B 17/22; A61B 17/22032; A61B 17/320758; A61B 17/320725; A61B 17/320783; A61M 25/10; A61M 25/104
See application file for complete search history.

(56) References Cited

U.S. PATENT DOCUMENTS 2,701,559 A    2/1955  Cooper
2,854,983 A    10/1958 Baskin
(Continued)

FOREIGN PATENT DOCUMENTS

CN    1688350 A    10/2005
CN    104689377 A   6/2015
(Continued)

OTHER PUBLICATIONS

Cremers et al. Comparison of Two Different Paclitaxel-Coated Balloon Catheters in the Porcine Coronary Restenosis Model; Clin Res Cardiol (2009) 98:325-350; DOI 10.1007/s00392-009-0008-2.
(Continued)

*Primary Examiner* — Vi X Nguyen

(57) ABSTRACT

Angioplasty and other dilatation devices are provided with scoring elements which incorporate a drug to be delivered to a body lumen, typically a blood vessel. The scoring elements have drugs and other active substances coated over a portion thereof or incorporated within internal structure of the element so that the drug is released into the luminal wall closely associated diseased regions of the body lumen as the scoring structure is radially expanded into the wall.

19 Claims, 17 Drawing Sheets

Related U.S. Application Data continuation of application No. 13/842,080, filed on Mar. 15, 2013, now Pat. No. 9,586,031, which is a division of application No. 11/411,635, filed on Apr. 26, 2006, now Pat. No. 10,076,641.

(60) Provisional application No. 60/680,450, filed on May 11, 2005.

(51) Int. Cl.

| | | |
|---|---|---|
| A61F 2/86 | (2013.01) | |
| A61F 2/958 | (2013.01) | |
| A61L 29/16 | (2006.01) | |
| A61B 17/3207 | (2006.01) | |
| A61M 5/00 | (2006.01) | |
| A61K 31/337 | (2006.01) | |
| A61L 29/08 | (2006.01) | |
| A61B 17/00 | (2006.01) | |

(52) U.S. Cl.
CPC .............. *A61F 2/86* (2013.01); *A61F 2/958* (2013.01); *A61K 31/337* (2013.01); *A61L 29/085* (2013.01); *A61L 29/16* (2013.01); *A61M 5/00* (2013.01); A61B 2017/00893 (2013.01); A61F 2210/0076 (2013.01); A61F 2230/0091 (2013.01); A61F 2250/0067 (2013.01); A61L 2300/00 (2013.01); A61L 2300/416 (2013.01); A61L 2420/06 (2013.01); A61M 2025/105 (2013.01); A61M 2025/1086 (2013.01)

(56) References Cited

U.S. PATENT DOCUMENTS

| | | | |
|---|---|---|---|
| 3,045,677 A | 7/1962 | Wallace | |
| 3,467,101 A | 9/1969 | Fogarty et al. | |
| 3,825,013 A | 7/1974 | Craven | |
| 4,327,736 A | 5/1982 | Inoue | |
| 4,456,011 A | 6/1984 | Warnecke | |
| 4,483,340 A | 11/1984 | Fogarty et al. | |
| 4,578,061 A | 3/1986 | Lemelson | |
| 4,604,762 A | 8/1986 | Robinson | |
| 4,637,396 A | 1/1987 | Cook | |
| 4,649,922 A | 3/1987 | Wiktor | |
| 4,723,549 A | 2/1988 | Wholey et al. | |
| 4,796,629 A | 1/1989 | Grayzel | |
| 4,838,853 A | 6/1989 | Parisi | |
| 4,887,613 A | 12/1989 | Farr et al. | |
| 4,895,166 A | 1/1990 | Farr et al. | |
| 4,921,484 A | 5/1990 | Hillstead | |
| 4,942,788 A | 7/1990 | Farr et al. | |
| 4,950,277 A | 8/1990 | Farr | |
| 4,956,830 A | 9/1990 | Mock et al. | |
| 4,966,604 A | 10/1990 | Reiss | |
| 4,969,458 A | 11/1990 | Wiktor | |
| 4,976,711 A | 12/1990 | Parins et al. | |
| 4,986,807 A | 1/1991 | Farr | |
| 4,986,830 A | 1/1991 | Owens et al. | |
| 4,998,539 A | 3/1991 | Delsanti | |
| 5,003,918 A | 4/1991 | Olson et al. | |
| 5,019,088 A | 5/1991 | Farr | |
| 5,019,089 A | 5/1991 | Farr | |
| 5,026,384 A | 6/1991 | Farr et al. | |
| 5,062,384 A | 11/1991 | Foley et al. | |
| 5,062,648 A | 11/1991 | Gomringer | |
| 5,071,407 A | 12/1991 | Termin et al. | |
| 5,098,440 A | 3/1992 | Hillstead | |
| 5,100,386 A | 3/1992 | Inoue | |
| 5,100,423 A | 3/1992 | Fearnot | |
| 5,101,682 A | 4/1992 | Radisch et al. | |
| 5,102,402 A | 4/1992 | Dror et al. | |
| 5,102,417 A | 4/1992 | Palmaz | |
| 5,108,416 A | 4/1992 | Ryan et al. | |
| 5,112,345 A | 5/1992 | Farr | |
| 5,116,318 A | 5/1992 | Hillstead | |
| 5,120,322 A | 6/1992 | Davis et al. | |
| 5,133,732 A * | 7/1992 | Wiktor .................. | A61F 2/88 623/1.22 |
| 5,176,693 A | 1/1993 | Pannek et al. | |
| 5,181,911 A | 1/1993 | Shturman | |
| 5,190,058 A | 3/1993 | Jones et al. | |
| 5,192,291 A | 3/1993 | Pannek et al. | |
| 5,196,024 A | 3/1993 | Barath | |
| 5,199,951 A | 4/1993 | Spears | |
| 5,209,727 A | 5/1993 | Radisch et al. | |
| 5,221,261 A | 6/1993 | Termin et al. | |
| 5,221,727 A | 6/1993 | Kumpf et al. | |
| 5,222,971 A | 6/1993 | Willard et al. | |
| 5,224,945 A | 7/1993 | Pannek et al. | |
| 5,224,949 A | 7/1993 | Gomringer et al. | |
| 5,226,887 A | 7/1993 | Farr et al. | |
| 5,243,997 A | 9/1993 | Uflacker et al. | |
| 5,263,963 A | 11/1993 | Garrison et al. | |
| 5,295,493 A | 3/1994 | Radisch et al. | |
| 5,295,959 A | 3/1994 | Gurbel et al. | |
| 5,304,121 A | 4/1994 | Sahatjian | |
| 5,306,250 A | 4/1994 | March et al. | |
| 5,308,354 A | 5/1994 | Zacca et al. | |
| 5,308,356 A | 5/1994 | Blackshear, Jr. et al. | |
| 5,318,576 A | 6/1994 | Plassche et al. | |
| 5,320,634 A | 6/1994 | Vigil et al. | |
| 5,336,178 A | 8/1994 | Kaplan et al. | |
| 5,336,234 A | 8/1994 | Vigil et al. | |
| 5,344,401 A | 9/1994 | Radisch et al. | |
| 5,344,419 A | 9/1994 | Spears | |
| 5,350,101 A | 9/1994 | Godlewski | |
| 5,354,279 A | 10/1994 | Hofling | |
| 5,370,614 A | 12/1994 | Amundson et al. | |
| 5,376,077 A | 12/1994 | Gomringer | |
| 5,419,777 A | 5/1995 | Hofling | |
| 5,423,745 A | 6/1995 | Todd et al. | |
| 5,443,078 A | 8/1995 | Uflacker | |
| 5,443,446 A | 8/1995 | Shturman | |
| 5,443,496 A | 8/1995 | Schwartz et al. | |
| 5,449,372 A | 9/1995 | Schmaltz et al. | |
| 5,449,373 A | 9/1995 | Pinchasik et al. | |
| 5,456,666 A | 10/1995 | Campbell et al. | |
| 5,456,667 A | 10/1995 | Ham et al. | |
| 5,458,568 A | 10/1995 | Racchini et al. | |
| 5,460,607 A | 10/1995 | Miyata et al. | |
| 5,470,314 A | 11/1995 | Walinsky | |
| 5,501,694 A | 3/1996 | Ressemann et al. | |
| 5,524,635 A | 6/1996 | Uflacker et al. | |
| 5,527,282 A | 6/1996 | Segal | |
| 5,536,178 A | 7/1996 | Novelli | |
| 5,538,504 A | 7/1996 | Linden et al. | |
| 5,545,132 A | 8/1996 | Fagan et al. | |
| 5,556,405 A | 9/1996 | Lary | |
| 5,556,408 A | 9/1996 | Farhat | |
| 5,562,620 A | 10/1996 | Klein et al. | |
| 5,569,195 A | 10/1996 | Saab | |
| 5,571,086 A | 11/1996 | Kaplan et al. | |
| 5,571,523 A | 11/1996 | Lee et al. | |
| 5,607,442 A | 3/1997 | Fischell et al. | |
| 5,609,574 A | 3/1997 | Kaplan et al. | |
| 5,616,149 A | 4/1997 | Barath | |
| 5,620,457 A | 4/1997 | Pinchasik et al. | |
| 5,624,433 A | 4/1997 | Radisch et al. | |
| 5,628,746 A | 5/1997 | Clayman | |
| 5,628,755 A | 5/1997 | Heller et al. | |
| 5,643,210 A | 7/1997 | Lacob | |
| 5,649,941 A | 7/1997 | Lary | |
| 5,681,281 A | 10/1997 | Vigil et al. | |
| 5,690,642 A | 11/1997 | Osborne et al. | |
| 5,695,469 A | 12/1997 | Segal | |
| 5,697,944 A | 12/1997 | Lary | |
| 5,697,971 A | 12/1997 | Fischell et al. | |
| 5,702,410 A | 12/1997 | Klunder et al. | |
| 5,707,385 A | 1/1998 | Williams | |
| 5,713,863 A | 2/1998 | Vigil et al. | |
| 5,713,913 A | 2/1998 | Lary et al. | |
| 5,730,698 A | 3/1998 | Fischell et al. | |

(56) References Cited

U.S. PATENT DOCUMENTS

| | | | |
|---|---|---|---|
| 5,733,303 A | 3/1998 | Israel et al. |
| 5,735,816 A | 4/1998 | Lieber et al. |
| 5,742,019 A | 4/1998 | Radisch et al. |
| 5,746,716 A | 5/1998 | Vigil et al. |
| 5,746,968 A | 5/1998 | Radisch et al. |
| 5,755,708 A | 5/1998 | Segal |
| 5,755,778 A | 5/1998 | Kleshinski |
| 5,755,781 A | 5/1998 | Jayaraman |
| 5,766,201 A | 6/1998 | Ravenscroft et al. |
| 5,766,238 A | 6/1998 | Lau et al. |
| 5,772,681 A | 6/1998 | Leoni |
| 5,776,141 A | 7/1998 | Klein et al. |
| 5,776,181 A | 7/1998 | Lee et al. |
| 5,779,698 A | 7/1998 | Clayman et al. |
| 5,792,144 A | 8/1998 | Fischell et al. |
| 5,792,415 A | 8/1998 | Hijlkema |
| 5,797,935 A | 8/1998 | Barath |
| 5,800,450 A | 9/1998 | Lary et al. |
| 5,807,355 A | 9/1998 | Ramzipoor et al. |
| 5,810,767 A | 9/1998 | Klein |
| 5,814,061 A | 9/1998 | Osborne et al. |
| 5,827,321 A | 10/1998 | Roubin et al. |
| 5,863,284 A | 1/1999 | Klein |
| 5,868,708 A | 2/1999 | Hart et al. |
| 5,868,719 A | 2/1999 | Tsukernik |
| 5,868,779 A | 2/1999 | Ruiz |
| 5,868,783 A | 2/1999 | Tower |
| 5,869,284 A | 2/1999 | Cao et al. |
| 5,873,852 A | 2/1999 | Vigil et al. |
| 5,891,090 A | 4/1999 | Thornton |
| 5,893,840 A | 4/1999 | Hull et al. |
| 5,902,475 A | 5/1999 | Trozera et al. |
| 5,904,679 A | 5/1999 | Clayman |
| 5,904,698 A | 5/1999 | Thomas et al. |
| 5,906,639 A | 5/1999 | Rudnick et al. |
| 5,916,166 A | 6/1999 | Reiss et al. |
| 5,919,200 A | 7/1999 | Stambaugh et al. |
| 5,954,742 A | 9/1999 | Osypka |
| 5,961,490 A | 10/1999 | Adams |
| 5,967,984 A | 10/1999 | Chu et al. |
| 5,980,486 A | 11/1999 | Enger |
| 5,987,661 A | 11/1999 | Peterson |
| 5,994,667 A | 11/1999 | Merdan et al. |
| 6,004,295 A | 12/1999 | Langer et al. |
| 6,013,055 A | 1/2000 | Bampos et al. |
| 6,036,686 A | 3/2000 | Griswold |
| 6,036,689 A | 3/2000 | Tu et al. |
| 6,036,708 A | 3/2000 | Sciver |
| 6,048,356 A | 4/2000 | Ravenscroft et al. |
| 6,053,913 A | 4/2000 | Tu et al. |
| 6,059,811 A | 5/2000 | Pinchasik et al. |
| 6,071,285 A | 6/2000 | Lashinski et al. |
| 6,071,286 A | 6/2000 | Mawad |
| 6,077,298 A | 6/2000 | Tu et al. |
| RE36,764 E | 7/2000 | Zacca et al. |
| 6,102,904 A | 8/2000 | Vigil et al. |
| 6,106,548 A | 8/2000 | Roubin et al. |
| 6,117,104 A | 9/2000 | Fitz |
| 6,117,153 A | 9/2000 | Lary et al. |
| 6,123,718 A | 9/2000 | Tu et al. |
| 6,129,706 A | 10/2000 | Janacek |
| 6,129,708 A | 10/2000 | Enger |
| 6,136,011 A | 10/2000 | Stambaugh |
| 6,146,323 A | 11/2000 | Fischell |
| 6,152,944 A | 11/2000 | Holman et al. |
| 6,156,254 A | 12/2000 | Andrews et al. |
| 6,156,265 A | 12/2000 | Sugimoto |
| 6,165,187 A | 12/2000 | Reger |
| 6,190,356 B1 | 2/2001 | Bersin |
| 6,190,403 B1 | 2/2001 | Fischell et al. |
| 6,193,686 B1 | 2/2001 | Estrada et al. |
| 6,197,013 B1 | 3/2001 | Reed et al. |
| 6,203,569 B1 | 3/2001 | Wijay |
| 6,206,910 B1 | 3/2001 | Berry et al. |
| 6,210,392 B1 | 4/2001 | Vigil et al. |
| 6,211,247 B1 | 4/2001 | Goodman |
| 6,224,625 B1 | 5/2001 | Jayaraman |
| 6,235,043 B1 | 5/2001 | Reiley et al. |
| 6,241,762 B1 | 6/2001 | Shanley |
| 6,245,040 B1 | 6/2001 | Inderbitzen et al. |
| 6,258,087 B1 | 7/2001 | Edwards et al. |
| 6,258,108 B1 | 7/2001 | Lary |
| 6,261,319 B1 | 7/2001 | Kveen et al. |
| 6,280,411 B1 | 8/2001 | Lennox |
| 6,283,947 B1 | 9/2001 | Mirzaee |
| 6,283,951 B1 | 9/2001 | Flaherty et al. |
| 6,287,336 B1 | 9/2001 | Globerman et al. |
| 6,289,568 B1 | 9/2001 | Miller et al. |
| 6,296,651 B1 | 10/2001 | Lary et al. |
| 6,299,604 B1 | 10/2001 | Ragheb et al. |
| 6,306,151 B1 | 10/2001 | Lary |
| 6,306,166 B1 | 10/2001 | Barry et al. |
| 6,309,414 B1 | 10/2001 | Rolando et al. |
| 6,312,459 B1 | 11/2001 | Huang et al. |
| 6,319,229 B1 | 11/2001 | Kim et al. |
| 6,319,230 B1 | 11/2001 | Palasis et al. |
| 6,319,242 B1 * | 11/2001 | Patterson ........... A61B 17/3207 |
| | | 604/508 |
| 6,319,251 B1 | 11/2001 | Tu et al. |
| 6,325,779 B1 | 12/2001 | Zedler |
| 6,325,813 B1 | 12/2001 | Hektner |
| 6,332,880 B1 | 12/2001 | Yang et al. |
| 6,355,013 B1 | 3/2002 | van Muiden |
| 6,355,059 B1 | 3/2002 | Richter et al. |
| 6,361,545 B1 | 3/2002 | Macoviak et al. |
| 6,364,856 B1 | 4/2002 | Ding et al. |
| 6,371,961 B1 | 4/2002 | Osborne et al. |
| 6,394,995 B1 | 5/2002 | Solar et al. |
| 6,415,009 B1 | 7/2002 | Toporov et al. |
| 6,416,494 B1 | 7/2002 | Wilkins |
| 6,416,539 B1 | 7/2002 | Hassdenteufel |
| 6,419,692 B1 | 7/2002 | Yang et al. |
| 6,425,882 B1 | 7/2002 | Vigil |
| 6,425,908 B2 | 7/2002 | Ravenscroft et al. |
| 6,440,158 B1 | 8/2002 | Saab |
| 6,447,501 B1 | 9/2002 | Solar et al. |
| 6,450,988 B1 | 9/2002 | Bradshaw |
| 6,450,989 B2 | 9/2002 | Dubrul et al. |
| 6,454,775 B1 | 9/2002 | Demarais et al. |
| 6,471,979 B2 | 10/2002 | New et al. |
| 6,475,233 B2 | 11/2002 | Trozera |
| 6,475,234 B1 | 11/2002 | Richter et al. |
| 6,475,236 B1 | 11/2002 | Roubin et al. |
| 6,478,807 B1 | 11/2002 | Foreman et al. |
| 6,500,186 B2 | 12/2002 | Lafontaine et al. |
| 6,515,099 B2 | 2/2003 | Sato et al. |
| 6,517,765 B1 | 2/2003 | Kelley |
| 6,540,722 B1 | 4/2003 | Boyle et al. |
| 6,551,310 B1 | 4/2003 | Ganz et al. |
| 6,554,795 B2 | 4/2003 | Bagaoisan et al. |
| 6,562,062 B2 | 5/2003 | Jenusaitis et al. |
| 6,565,528 B1 | 5/2003 | Mueller |
| 6,569,180 B1 | 5/2003 | Sirhan et al. |
| 6,575,993 B1 | 6/2003 | Yock |
| 6,592,548 B2 | 7/2003 | Jayaraman |
| 6,602,281 B1 | 8/2003 | Klein |
| 6,605,107 B1 | 8/2003 | Klein |
| 6,607,442 B2 | 8/2003 | Ogata et al. |
| 6,613,072 B2 | 9/2003 | Lau et al. |
| 6,616,650 B1 | 9/2003 | Rowe |
| 6,616,678 B2 | 9/2003 | Nishtala et al. |
| 6,626,861 B1 | 9/2003 | Hart et al. |
| 6,632,231 B2 | 10/2003 | Radisch et al. |
| 6,648,912 B2 | 11/2003 | Trout et al. |
| 6,652,548 B2 | 11/2003 | Evans et al. |
| 6,656,156 B2 | 12/2003 | Yang et al. |
| 6,656,351 B2 | 12/2003 | Boyle |
| 6,663,660 B2 | 12/2003 | Dusbabek et al. |
| 6,682,545 B1 | 1/2004 | Kester |
| 6,695,813 B1 | 2/2004 | Boyle et al. |
| 6,730,064 B2 | 5/2004 | Ragheb et al. |
| 6,743,196 B2 | 6/2004 | Barbut et al. |
| 6,746,463 B1 | 6/2004 | Schwartz |
| 6,783,542 B2 | 8/2004 | Eidenschink |

(56) References Cited

U.S. PATENT DOCUMENTS

| | | |
|---|---|---|
| 6,840,950 B2 | 1/2005 | Stanford et al. |
| 6,872,206 B2 | 3/2005 | Edwards et al. |
| 6,918,920 B1 | 7/2005 | Wang et al. |
| 6,939,320 B2 | 9/2005 | Lennox |
| 6,942,680 B2 | 9/2005 | Grayzel et al. |
| 6,951,566 B2 | 10/2005 | Lary |
| 7,011,654 B2 | 3/2006 | Dubrul et al. |
| 7,011,670 B2 | 3/2006 | Radisch et al. |
| 7,029,483 B2 | 4/2006 | Schwartz |
| 7,060,051 B2 | 6/2006 | Palasis |
| 7,108,684 B2 | 9/2006 | Farnan |
| 7,131,981 B2 | 11/2006 | Appling et al. |
| 7,172,609 B2 | 2/2007 | Radisch et al. |
| 7,186,237 B2 | 3/2007 | Meyer et al. |
| 7,232,432 B2 | 6/2007 | Fulton et al. |
| 7,303,572 B2 | 12/2007 | Melsheimer et al. |
| 7,354,445 B2 | 4/2008 | Nicholson et al. |
| 7,357,813 B2 | 4/2008 | Burgermeister |
| 7,396,358 B2 | 7/2008 | Appling et al. |
| 7,445,792 B2 | 11/2008 | Toner et al. |
| 7,445,795 B2 | 11/2008 | Bakhshaee et al. |
| 7,455,652 B2 | 11/2008 | Laird |
| 7,465,311 B2 | 12/2008 | Wang et al. |
| 7,494,497 B2 | 2/2009 | Weber |
| 7,517,352 B2 | 4/2009 | Evans et al. |
| 7,524,319 B2 | 4/2009 | Dubrul |
| 7,566,319 B2 | 7/2009 | McAuley et al. |
| 7,686,824 B2 | 3/2010 | Konstantino et al. |
| 7,691,119 B2 | 4/2010 | Farnan |
| 7,708,748 B2 | 5/2010 | Weisenburgh, II et al. |
| 7,708,753 B2 | 5/2010 | Hardert |
| 7,736,375 B2 | 6/2010 | Crow |
| 7,763,043 B2 | 7/2010 | Goodin et al. |
| 7,780,715 B2 | 8/2010 | Shaked et al. |
| 7,780,798 B2 | 8/2010 | Stinson et al. |
| 7,803,149 B2 | 9/2010 | Bates et al. |
| 7,811,622 B2 | 10/2010 | Bates et al. |
| 7,875,284 B2 | 1/2011 | Reyes et al. |
| 7,931,663 B2 | 4/2011 | Farnan et al. |
| 7,955,350 B2 | 6/2011 | Konstantino et al. |
| 7,963,942 B2 | 6/2011 | Chen |
| 7,976,557 B2 | 7/2011 | Kunis |
| 7,998,184 B2 | 8/2011 | Eidenschink |
| 8,043,259 B2 | 10/2011 | Radisch et al. |
| 8,052,703 B2 | 11/2011 | St. Martin et al. |
| 8,066,726 B2 | 11/2011 | Kelley |
| 8,080,026 B2 | 12/2011 | Konstantino et al. |
| 8,123,770 B2 | 2/2012 | Olsen et al. |
| 8,192,675 B2 | 6/2012 | Burton et al. |
| 8,221,444 B2 | 7/2012 | Wang et al. |
| 8,323,307 B2 | 12/2012 | Hardert |
| 8,348,987 B2 | 1/2013 | Eaton |
| 8,382,820 B2 | 2/2013 | Addonizio et al. |
| 8,454,636 B2 | 6/2013 | Konstantino et al. |
| 8,454,637 B2 | 6/2013 | Aggerholm et al. |
| 8,574,248 B2 | 11/2013 | Kassab |
| 8,673,387 B2 | 3/2014 | Bates et al. |
| 8,685,050 B2 | 4/2014 | Schur et al. |
| 8,685,990 B2 | 4/2014 | Coats et al. |
| 8,721,667 B2 | 5/2014 | Konstantino et al. |
| 8,864,743 B2 | 10/2014 | Konstantino et al. |
| 9,011,896 B2 | 4/2015 | Speck et al. |
| 9,072,812 B2 | 7/2015 | Speck et al. |
| 9,078,951 B2 | 7/2015 | Speck et al. |
| 9,101,684 B2 | 8/2015 | Speck et al. |
| 9,173,977 B2 | 11/2015 | Speck et al. |
| 9,586,031 B2 | 3/2017 | Konstantino et al. |
| 2001/0001113 A1 | 5/2001 | Lim et al. |
| 2001/0001823 A1 | 5/2001 | Ryan |
| 2001/0007082 A1 | 7/2001 | Dusbabek et al. |
| 2001/0012950 A1 | 8/2001 | Nishtala et al. |
| 2001/0016753 A1 | 8/2001 | Caprio et al. |
| 2002/0010487 A1 | 1/2002 | Evans et al. |
| 2002/0010489 A1 | 1/2002 | Grayzel et al. |
| 2002/0029015 A1 | 3/2002 | Camenzind et al. |
| 2002/0037358 A1 | 3/2002 | Barry et al. |
| 2002/0038144 A1 | 3/2002 | Trout et al. |
| 2002/0045930 A1 | 4/2002 | Burg et al. |
| 2002/0065548 A1 | 5/2002 | Birdsall et al. |
| 2002/0091438 A1 | 7/2002 | Trozera |
| 2002/0111633 A1 | 8/2002 | Stoltze et al. |
| 2002/0165599 A1 | 11/2002 | Nasralla |
| 2002/0193873 A1 | 12/2002 | Brucker et al. |
| 2003/0018376 A1 | 1/2003 | Solar et al. |
| 2003/0023200 A1 | 1/2003 | Barbut et al. |
| 2003/0028235 A1 | 2/2003 | McIntosh et al. |
| 2003/0032973 A1 | 2/2003 | Jenusaitis et al. |
| 2003/0065381 A1 | 4/2003 | Solar et al. |
| 2003/0074046 A1 | 4/2003 | Richter |
| 2003/0078606 A1 | 4/2003 | Lafontaine et al. |
| 2003/0097169 A1 | 5/2003 | Brucker et al. |
| 2003/0105509 A1 | 6/2003 | Jang et al. |
| 2003/0114915 A1 | 6/2003 | Mareiro et al. |
| 2003/0144683 A1 | 7/2003 | Sirhan et al. |
| 2003/0149468 A1 | 8/2003 | Wallsten |
| 2003/0152870 A1 | 8/2003 | Huang |
| 2003/0153870 A1 | 8/2003 | Meyer et al. |
| 2003/0171799 A1 | 9/2003 | Lee et al. |
| 2003/0187494 A1 | 10/2003 | Loaldi |
| 2003/0195609 A1 | 10/2003 | Berenstein et al. |
| 2003/0199970 A1 | 10/2003 | Shanley |
| 2003/0199988 A1 | 10/2003 | Devonec et al. |
| 2003/0208244 A1 | 11/2003 | Stein et al. |
| 2003/0208255 A1 | 11/2003 | O'Shaughnessy et al. |
| 2003/0229370 A1 | 12/2003 | Miller |
| 2004/0034384 A1 | 2/2004 | Fukaya |
| 2004/0106975 A1 | 6/2004 | Solovay et al. |
| 2004/0111108 A1 | 6/2004 | Faman |
| 2004/0127475 A1 | 7/2004 | New et al. |
| 2004/0133223 A1 | 7/2004 | Weber |
| 2004/0143287 A1 | 7/2004 | Konstantino et al. |
| 2004/0193257 A1 | 9/2004 | Wu et al. |
| 2004/0208985 A1 | 10/2004 | Rowan et al. |
| 2004/0210299 A1 | 10/2004 | Rogers et al. |
| 2004/0230293 A1 | 11/2004 | Yip et al. |
| 2004/0243158 A1 | 12/2004 | Konstantino et al. |
| 2005/0010278 A1 | 1/2005 | Vardi et al. |
| 2005/0021070 A1 | 1/2005 | Feld et al. |
| 2005/0021071 A1 | 1/2005 | Konstantino et al. |
| 2005/0033417 A1 | 2/2005 | Borges et al. |
| 2005/0037048 A1 | 2/2005 | Song |
| 2005/0070888 A1 | 3/2005 | DiMatteo et al. |
| 2005/0080478 A1 | 4/2005 | Barongan |
| 2005/0083768 A1 | 4/2005 | Hara |
| 2005/0119723 A1 | 6/2005 | Peacock |
| 2005/0131512 A1 | 6/2005 | Vonderwalde |
| 2005/0137690 A1 | 6/2005 | Salahieh et al. |
| 2005/0271844 A1 | 12/2005 | Mapes et al. |
| 2005/0278021 A1 | 12/2005 | Bates et al. |
| 2005/0288629 A1 | 12/2005 | Kunis |
| 2006/0004323 A1 | 1/2006 | Chang et al. |
| 2006/0015133 A1 | 1/2006 | Grayzel et al. |
| 2006/0020243 A1 | 1/2006 | Speck et al. |
| 2006/0074484 A1 | 4/2006 | Huber |
| 2006/0085025 A1 | 4/2006 | Faman et al. |
| 2006/0111736 A1 | 5/2006 | Kelley |
| 2006/0112536 A1 | 6/2006 | Herweck et al. |
| 2006/0129093 A1 | 6/2006 | Jackson |
| 2006/0149308 A1 | 7/2006 | Melsheimer et al. |
| 2006/0173487 A1 | 8/2006 | Uflacker et al. |
| 2006/0184191 A1 | 8/2006 | O'Brien |
| 2006/0240014 A1 | 10/2006 | Sukhatme |
| 2006/0247674 A1 | 11/2006 | Roman |
| 2006/0259005 A1 | 11/2006 | Konstantino et al. |
| 2006/0259062 A1 | 11/2006 | Konstantino |
| 2006/0270193 A1 | 11/2006 | Hidaka et al. |
| 2007/0020380 A1 | 1/2007 | Ding |
| 2007/0037739 A1 | 2/2007 | Wang et al. |
| 2007/0112422 A1 | 5/2007 | Dehdashtian |
| 2007/0128242 A1 | 6/2007 | Zhao |
| 2007/0185513 A1 | 8/2007 | Woolfson et al. |
| 2007/0190103 A1 | 8/2007 | Hossainy et al. |
| 2007/0198047 A1 | 8/2007 | Schon et al. |
| 2007/0212394 A1 | 9/2007 | Reyes et al. |

(56) References Cited

U.S. PATENT DOCUMENTS

| | | |
|---|---|---|
| 2007/0213808 A1 | 9/2007 | Roubin et al. |
| 2008/0021385 A1 | 1/2008 | Barry et al. |
| 2008/0118544 A1 | 5/2008 | Wang |
| 2008/0181927 A1 | 7/2008 | Zhao |
| 2008/0241215 A1 | 10/2008 | Falotico et al. |
| 2008/0300610 A1 | 12/2008 | Chambers |
| 2009/0105686 A1 | 4/2009 | Snow et al. |
| 2009/0105687 A1 | 4/2009 | Deckman et al. |
| 2009/0136560 A1 | 5/2009 | Bates et al. |
| 2009/0246252 A1 | 10/2009 | Arps et al. |
| 2009/0246253 A1 | 10/2009 | Ding |
| 2009/0264859 A1 | 10/2009 | Mas |
| 2009/0281490 A1 | 11/2009 | McAuley et al. |
| 2009/0306582 A1 | 12/2009 | Granada et al. |
| 2010/0042121 A1 | 2/2010 | Schneider et al. |
| 2010/0121372 A1 | 5/2010 | Farnan |
| 2010/0179647 A1 | 7/2010 | Carpenter et al. |
| 2010/0209472 A1 | 8/2010 | Wang |
| 2010/0233228 A1 | 9/2010 | Speck |
| 2010/0233236 A1 | 9/2010 | Zhao |
| 2010/0278997 A1 | 11/2010 | Speck et al. |
| 2010/0285085 A1 | 11/2010 | Stankus et al. |
| 2010/0286720 A1 | 11/2010 | Shaked et al. |
| 2010/0286721 A1 | 11/2010 | Goodin et al. |
| 2010/0324645 A1 | 12/2010 | Stankus et al. |
| 2011/0054396 A1 | 3/2011 | Kangas et al. |
| 2011/0082483 A1 | 4/2011 | Diamant et al. |
| 2011/0125247 A1 | 5/2011 | Farnan et al. |
| 2011/0143014 A1 | 6/2011 | Stankus et al. |
| 2011/0160756 A1 | 6/2011 | Aggerholm et al. |
| 2011/0196340 A1 | 8/2011 | Barry et al. |
| 2011/0230818 A1 | 9/2011 | Kunis |
| 2011/0264039 A1 | 10/2011 | Thielen et al. |
| 2011/0270177 A1 | 11/2011 | Chambers et al. |
| 2011/0295200 A1 | 12/2011 | Speck et al. |
| 2012/0059401 A1 | 3/2012 | Konstantino et al. |
| 2012/0172787 A1 | 7/2012 | McClain et al. |
| 2012/0215251 A1 | 8/2012 | Burton et al. |
| 2012/0239001 A1 | 9/2012 | Barry et al. |
| 2012/0277626 A1 | 11/2012 | Burbank et al. |
| 2013/0023817 A1 | 1/2013 | Speck et al. |
| 2013/0037777 A1 | 2/2013 | Mikawa et al. |
| 2013/0041315 A1 | 2/2013 | Speck |
| 2013/0041391 A1 | 2/2013 | Spencer et al. |
| 2013/0041399 A1 | 2/2013 | Hardert |
| 2013/0046237 A1 | 2/2013 | Speck et al. |
| 2013/0060127 A1 | 3/2013 | Burton et al. |
| 2013/0066346 A1 | 3/2013 | Pigott |
| 2013/0096604 A1 | 4/2013 | Hanson et al. |
| 2013/0150874 A1 | 6/2013 | Kassab |
| 2013/0211381 A1 | 8/2013 | Feld |
| 2013/0218181 A1 | 8/2013 | Feld et al. |
| 2013/0231638 A1 | 9/2013 | Speck et al. |
| 2014/0058358 A1 | 2/2014 | Kassab |
| 2014/0066960 A1 | 3/2014 | Feld et al. |
| 2014/0128801 A1 | 5/2014 | Speck et al. |
| 2014/0257181 A1 | 9/2014 | Speck |
| 2015/0297797 A1 | 10/2015 | Speck et al. |

FOREIGN PATENT DOCUMENTS

| | | | |
|---|---|---|---|
| EP | 0565796 B1 | 5/1997 |
| EP | 0623315 B1 | 6/1999 |
| EP | 1169970 A1 | 1/2002 |
| EP | 1179323 A2 | 2/2002 |
| EP | 0832608 B1 | 3/2003 |
| EP | 1042997 B1 | 3/2005 |
| EP | 1581298 B1 | 8/2006 |
| EP | 1414373 B1 | 5/2008 |
| EP | 1337198 B1 | 6/2009 |
| EP | 1748816 B1 | 7/2010 |
| EP | 2063924 B1 | 10/2010 |
| EP | 2283890 A1 | 2/2011 |
| EP | 1962696 B1 | 3/2012 |
| EP | 1737530 B1 | 3/2013 |
| EP | 2564890 A1 | 3/2013 |
| EP | 2886136 A1 | 6/2015 |
| EP | 2886137 A1 | 6/2015 |
| JP | 2002126086 A | 5/2002 |
| JP | 2002126086 A1 | 5/2002 |
| JP | 2004148013 A1 | 5/2004 |
| JP | 2008504059 A | 5/2005 |
| JP | 2005343897 A | 12/2005 |
| JP | 5745030 B2 | 6/2013 |
| WO | WO1991002494 A1 | 3/1991 |
| WO | 9217118 A1 | 10/1992 |
| WO | WO1993001753 A2 | 2/1993 |
| WO | WO1994010919 A1 | 5/1994 |
| WO | 1994023787 A1 | 10/1994 |
| WO | WO1994023787 A1 | 10/1994 |
| WO | WO1994024946 A1 | 11/1994 |
| WO | WO1995003083 A1 | 2/1995 |
| WO | WO1998005377 A1 | 2/1998 |
| WO | WO1998045506 A1 | 10/1998 |
| WO | 1999017680 A1 | 4/1999 |
| WO | 1999055253 A1 | 11/1999 |
| WO | 1999062430 A1 | 12/1999 |
| WO | 02083011 A1 | 10/2002 |
| WO | 2002076509 A2 | 10/2002 |
| WO | WO2002083011 A1 | 10/2002 |
| WO | WO2003026536 A1 | 4/2003 |
| WO | WO2003039628 A2 | 5/2003 |
| WO | WO2003041760 A2 | 5/2003 |
| WO | 2004022124 A1 | 3/2004 |
| WO | 2004028582 A1 | 4/2004 |
| WO | WO2004028610 A2 | 4/2004 |
| WO | WO2004060460 A2 | 7/2004 |
| WO | WO2004066852 A2 | 8/2004 |
| WO | 2004108130 A1 | 12/2004 |
| WO | WO2005025458 A1 | 3/2005 |
| WO | 2006007173 A1 | 1/2006 |
| WO | 2009018816 A2 | 2/2009 |
| WO | 2009066330 A1 | 5/2009 |
| WO | 2009155405 A1 | 12/2009 |
| WO | 2013177175 A8 | 11/2013 |

OTHER PUBLICATIONS

EP Examination Report dated Oct. 9, 2013 from corresponding EP Application No. 10775805.4, 6 pages.
European Search Opinion issued in EP Application No. 15154222, dated May 18, 2015, 5 pages.
European search report and search opinion dated May 4, 2010 for EP 06770116.9.
European search report and search opinion dated Dec. 28, 2009 for EP 05792875.6.
European Search Report issued in EP Application No. 15154222 dated May 18, 2015. 2 pages.
Extended European Search Report issued in EP Application No. 11827369.7, dated Apr. 7, 2014. 6 pages.
File History for U.S. Appl. No. 11/411,635, filed Apr. 26, 2006.
File History for U.S. Appl. No. 13/044,425, filed Mar. 9, 2011.
File History for U.S. Appl. No. 13/842,080, filed Mar. 15, 2013.
First Examination Report dated Feb. 5, 2014 from corresponding EP Application No. 05733012.8.
International search report and written opinion dated Feb. 27, 2007 for PCT/US2006/017872.
International search report and written opinion dated May 23, 2006 for PCT /2005/009571.
International search report and written opinion dated Jul. 26, 2007 for PCT/2005/028809.
International search report and written opinion dated Nov. 4, 2004 for PCT/2004/000177.
International Search Report and Written Opinion issued in PCT Application No. PCTEP2010066754 dated May 1, 2011,11 pages.
International Search Report and Written Opinion issued in PCT/US2011/052392 dated Jan. 11, 2012, 7 pages.
International Search Report issued in PCT/US2002/035547dated May 20, 2003,3 Pages.
International Search Report issued in PCT/US2004/027836 dated Dec. 30, 2004,1 Page.

(56) References Cited

OTHER PUBLICATIONS

Japanese office action dated Jul. 9, 2010 for JP 2007-505113. (in Japanese with English translation).
Notification of Office Action dated Aug. 14, 2014 from corresponding JP Application No. 2013-505347.
Notification of the First Office Action dated Jan. 16, 2014, from corresponding Chinese Application No. 201080066293.3.
Scheller et al. Paclitaxel Balloon Coating, a Novel Method for Prevention and Therapy of Restenosis; Circulation. 2004;110:810-814, Aug. 9, 2004.
Supplementary European Search Report dated Nov. 20, 2013 from corresponding EP Application No. 35733012.8.
Suzuki et al. Anti-Oxidants for Therapeutic Use: Why Are Only a Few Drugs in Clinical Use? Advanced Drug Delivery Reviews, vol. 61, 2009, pp. 287-289.
*Trireme Medical, LLC* v. *AngioScore, Inc.*, Decision on Appeal dated Feb. 5, 2016, United States Court of Appeals tor the Federal Circuit, Case No. 2015-1504.
*Trireme Medical, LLC.* v. *Angioscore, Inc.*, Answer to Complaint filed in the United States District Court, Northern District of California on Aug. 18, 2014, Case No. 14-cv-02946-LB.
*Trireme Medical, LLC.* v. *Angioscore, Inc.*, Complaint for Correction of Inventorship filed in the United States District Court, Northern District of California on Jun. 25, 2014, Case No. 14-cv-02946-LB.
*Trireme Medical, LLC.* v. *Angioscore, Inc.*, Defendant Angioscore's Notice of Motion and Motion to Dismiss filed in the United States District Court, Northern District of California on Jan. 29, 2015, Case No. 14-cv-02946-LB.
*Trireme Medical, LLC.* v. *Angioscore, Inc.*, Judgement entered in the United States District Court, Northern District of California on Mar. 31, 2015, Case No. 14-CV-02946-LB.
*Trireme Medical, LLC.* v. *Angioscore, Inc.*, Notice of Appeal filed in the United States District Court, Northern District of California on Mar. 20, 2015, Case No. 14-CV-02946-LB.
*Trireme Medical, LLC.* v. *Angioscore, Inc.*, Notice of Docketing entered in the United States District Court, Northern District of California on Apr. 1, 2015, Case No. 14-cv-02946-LB.
*Trireme Medical, LLC.* v. *Angioscore, Inc.*, Opposition to Defendant Angioscore's Motion to Dismiss filed in the United States District Court, Northern District of California on Feb. 12, 2015, Case No. 14-cv-02946-LB.
*Trireme Medical, LLC.* v. *Angioscore, Inc.*, Order Granting Motion to Dismiss entered in the United States District Court, Northern District of California on Mar. 17, 2015, Case No. 14-cv-02946-LB.
*Trireme Medical, LLC.* v. *Angioscore, Inc.*, Reply in Support of Angioscore's Motion to Dismiss filed in the United States District Court, Northern District of California on Feb. 19, 2015, Case No. 14-cv-02946-LB.

\* cited by examiner

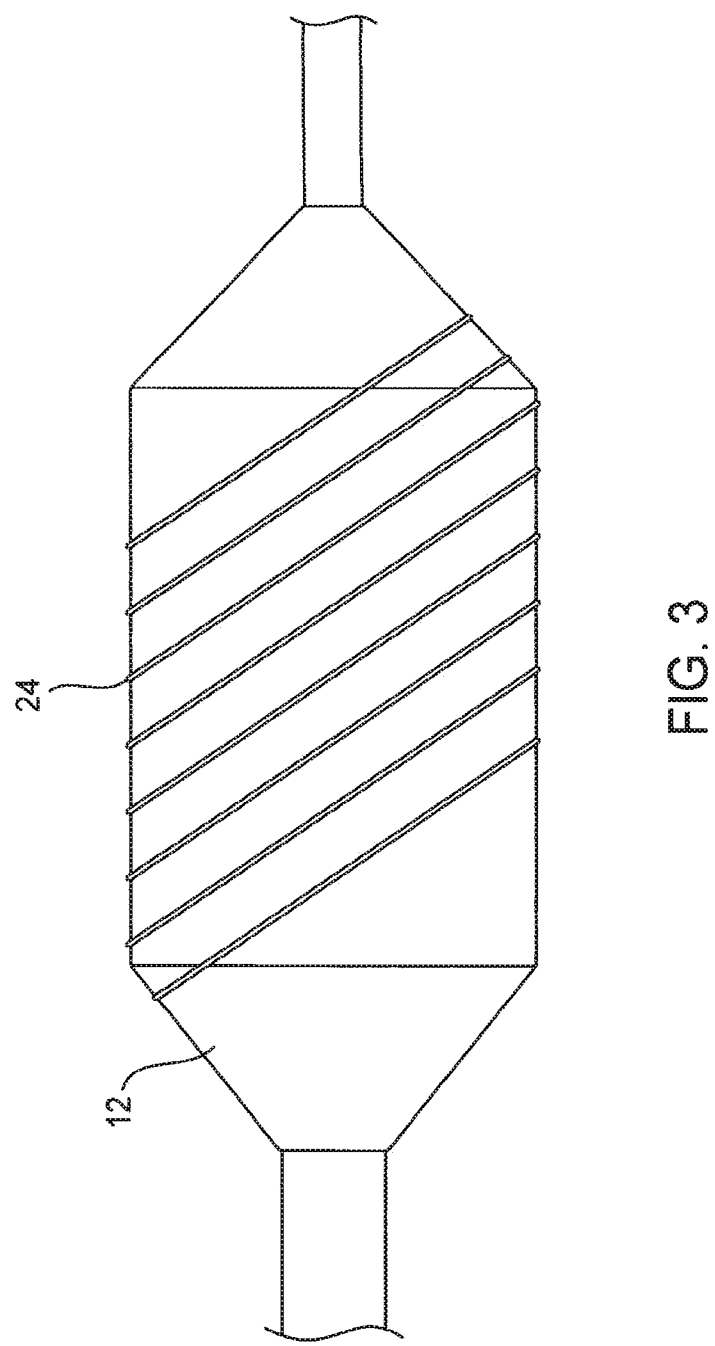

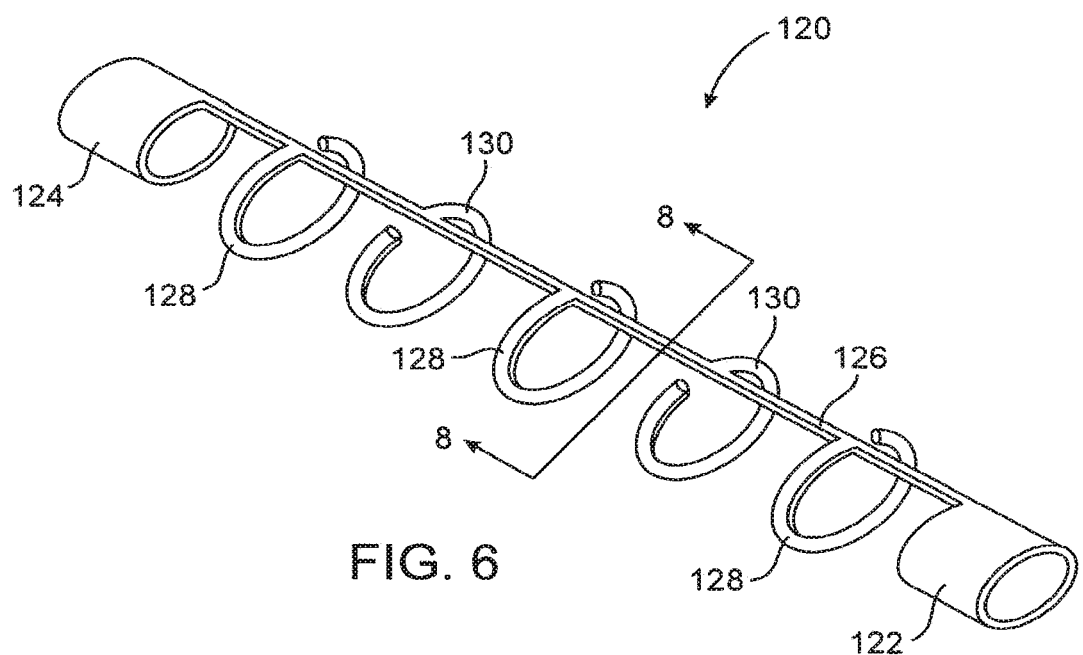
FIG. 6
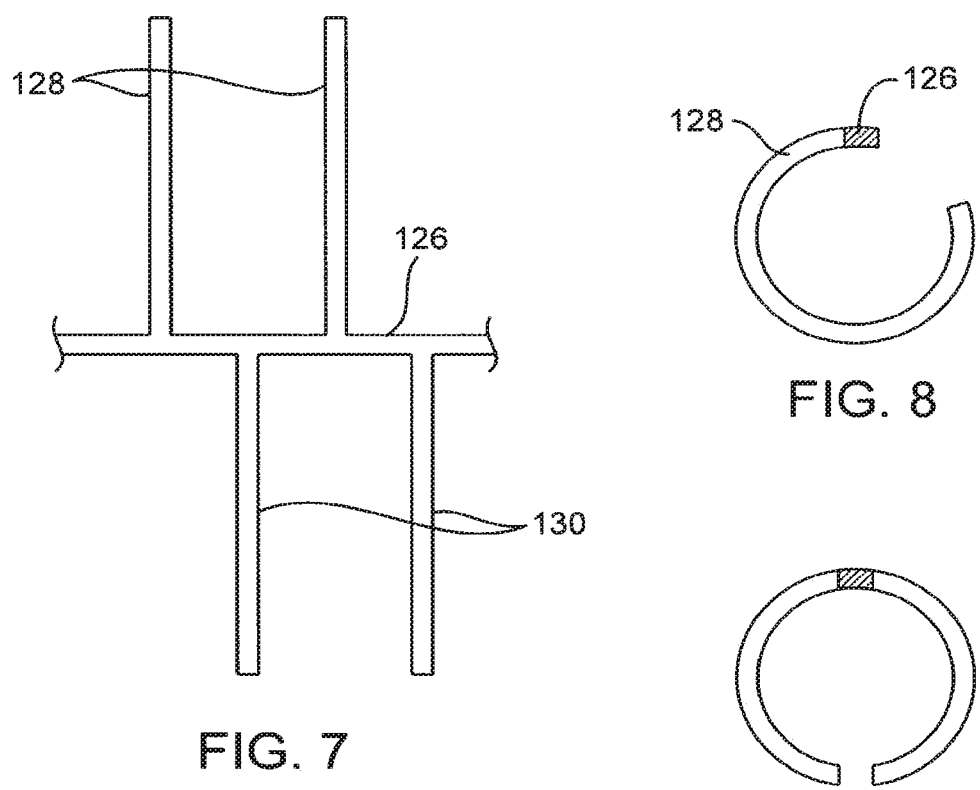
FIG. 7
FIG. 8
FIG. 9

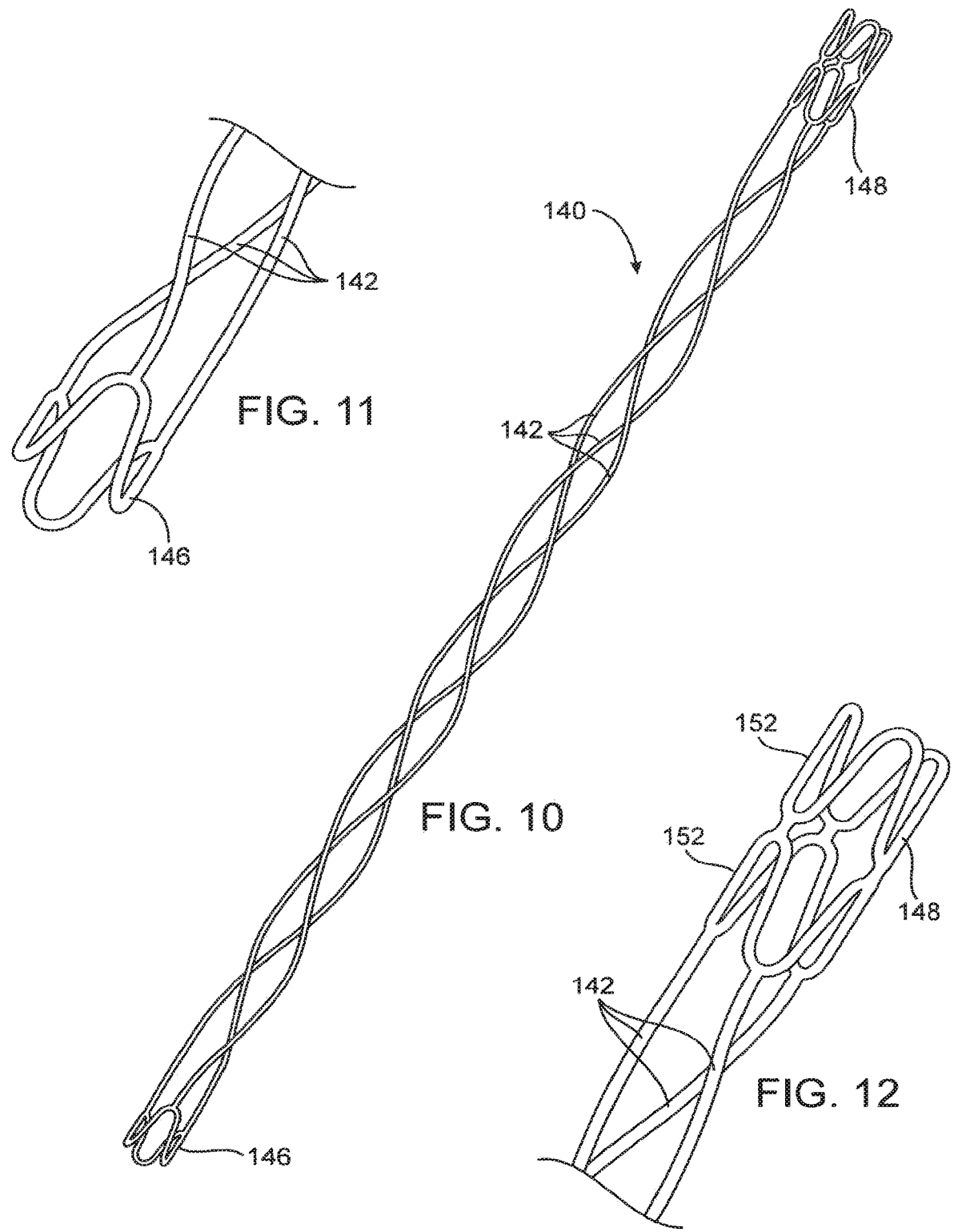

METHODS AND SYSTEMS FOR DELIVERING SUBSTANCES INTO LUMINAL WALLS

RELATED APPLICATIONS

The present application claims the benefit of and is a continuation of U.S. patent application Ser. No. 15/431,302, filed Feb. 13, 2017, which is a continuation of U.S. patent application Ser. No. 13/842,080, filed Mar. 15, 2013, now U.S. Pat. No. 9,856,031, which is a divisional of U.S. patent application Ser. No. 11/411,635, filed Apr. 26, 2006, now U.S. Pat. No. 10,076,641, which is a non-provisional of U.S. Patent Application Ser. No. 60/680,450, filed May 11, 2005. The full disclosure of each of the above applications is incorporated herein by reference for all purposes.

BACKGROUND OF THE INVENTION

1. Field of the Invention

The present invention relates to the field of medical devices, more specifically medical to devices intended to treat stenoses in the vascular system.

Balloon dilatation (angioplasty) is a common medical procedure mainly directed at revascularization of stenotic vessels by inserting a catheter having a dilatation balloon through the vascular system. The balloon is inflated inside a stenosed region in a blood vessel in order to apply radial pressure to the inner wall of the vessel and widen the stenosed region to enable better blood flow.

In many cases, the balloon dilatation procedure is immediately followed by a stenting procedure where a stent is placed to maintain vessel patency following the angioplasty. Failure of the angioplasty balloon to properly widen the stenotic vessel, however, may result in improper positioning of the stent in the blood vessel. If a drug-eluting stent is used, its effectiveness may be impaired by such improper positioning and the resulting restenosis rate may be higher. This is a result of several factors, including the presence of gaps between the stent and the vessel wall, calcified areas that were not treated properly by the balloon, and others.

Conventional balloon angioplasty suffers from a number of other shortcomings as well. In some cases the balloon dilatation procedure causes damage to the blood vessel due to aggressive balloon inflation that may stretch the diseased vessel beyond its elastic limits. Such over inflation may damage the vessel wall and lead to restenosis of the section that was stretched by the balloon. In other cases, slippage of the balloon during the dilatation procedure may occur. This may result in injury to the vessel wall surrounding the treated lesion. One procedure in which slippage is likely to happen is during treatment of in-stent restenosis, which at present is difficult to treat by angioplasty balloons. Fibrotic lesions are also hard to treat with conventional balloons, and elastic recoil is usually observed after treatment of these lesions. Many long lesions have fibrotic sections that are difficult to treat using angioplasty balloons.

To overcome at least some of these problems these problems, U.S. Pat. No. 5,320,634 describes the addition of cutting blades to the balloon. The blades can cut the lesions as the balloon is inflated. U.S. Pat. No. 5,616,149 describes a similar method of attaching sharp cutting edges to the balloon. U.S. Patent Publication 2003/0032973 describes a stent-like structure having non-axial grips for securing an angioplasty balloon during inflation. U.S. Pat. No. 6,129,706 describes a balloon catheter having bumps on its outer surface. U.S. Pat. No. 6,394,995 describes a method of reducing the balloon profile to allow crossing of tight lesions. U.S. Patent Publication 2003/0153870 describes a balloon angioplasty catheter having a flexible elongate elements that create longitudinal channels in a lesion or stenosis.

While the use of angioplasty balloons having cutting blades has proved to be a significant advantage under many circumstances, the present cutting balloon designs and methods for their use continue to suffer from shortcomings. Most commercial cutting balloon designs, including those available from INTERVENTIONAL TECHNOLOGIES, INC., of San Diego, Calif., now owned by BOSTON SCIENTIFIC, of Natick, Mass., have relatively long, axially aligned blades carried on the outer surface of an angioplasty balloon. Typically, the blades are carried on a relatively rigid base directly attached to the outer balloon surface. The addition of such rigid, elongated blade structures makes the balloon itself quite stiff and limits the ability to introduce the balloon through torturous regions of the vasculature, particularly the smaller vessels within the coronary vasculature. Moreover, the cutting balloons can be difficult to deflate and collapse, making removal of the balloons from the vasculature more difficult than with corresponding angioplasty balloons which do not include cutting blades. Additionally, the axially oriented cuts imparted by such conventional cutting balloons do not always provide the improved dilatation and treatment of fibrotic lesions which would be desired.

In addition to the above, drug eluting stents (DES), although very successful, are not suitable for every patient. Patients undergoing DES implantation are kept under a regimen of anti-coagulant therapy for an extended period of time to minimize risk of late thrombosis. Anticoagulants may cause excessive bleeding and are not recommended for people who are suffering from certain other health problems and/or who might need surgery. Some patients are intolerant to anticoagulants.

For all of these reasons, it would be desirable to provide improved methods, catheters, and systems for performing angioplasty and other vascular interventions for treating vascular occlusive diseases, including but not limited to treatment of hardened and calcified plaque. It would be particularly desirable if such methods and systems could be utilized for other body lumens beyond the vasculature. In particular, it would be desirable to provide methods and systems which could utilize both conventional and novel balloon scoring and cutting structures for delivering therapeutic agents to blood vessels and other body lumens. Such methods and systems could thus disrupt vascular and luminal occlusions in a manner provided by conventional scoring and cutting structures while simultaneously delivering therapeutic agents to the blood vessel, and more particularly to the intimal and subintimal regions of the blood vessel which can be accessed by the cutting element in order to enhance distribution of the therapeutic agents. At least some of these objectives will be met by the inventions described hereinbelow

2. Description of the Background Art

The following U.S. patents and printed publication relate to cutting balloons and balloon structures: U.S. Pat. Nos. 6,450,988; 6,425,882; 6,394,995; 6,355,013; 6,245,040; 6,210,392; 6,190,356; 6,129,706; 6,123,718; 5,891,090; 5,797,935; 5,779,698; 5,735,816; 5,624,433; 5,616,149; 5,545,132; 5,470,314; 5,320,634; 5,221,261; 5,196,024; and Published U.S. Pat. App. 2003/0032973. Other U.S. patents of interest include U.S. Pat. Nos. 6,454,775; 5,100,423, 4,998,539; 4,969,458; and 4,921,984. The following patents describe drug delivery catheters having needle based delivery mechanisms: U.S. Pat. No. 4,578,061, describes needle injection catheters having deflectable, axially advanceable needles. U.S. Pat. No. 5,538,504, describes a needle injection catheter having a transversely oriented needle that is laterally advanced by a balloon driver. Also of interest are U.S. Pat. Nos. 6,319,230; 6,283,951; 6,283,947; 6,004,295; 5,419,777; and 5,354,279. Drug coated stents and angioplasty balloons are described in numerous patents and published applications including U.S. Pat. Nos. 6,280,411; 6,656,156; 6,682,545; and Publication Nos. US2004/ 0193257; US2004/0208985; and US2005/0033417.

BRIEF SUMMARY OF THE INVENTION

The present invention provides methods and apparatus for delivering active substances to luminal sites, and in particular for delivering anti-hyperplasia substances to diseased sites in a patient's vascular system, such as sites of thrombosis and plaque in a patient's arteries. Methods for delivering active substance to a luminal site comprise positioning a scoring element within the body lumen and advancing the scoring element to score a wall of the body lumen. The scoring element comprises the active substance to be delivered to the luminal site. By initially scoring an exposed surface of the luminal wall or a lesion, the active substance can be released to locations in or beneath the intimal layer of the vessel wall, typically to a depth in the range from 0.001 mm to 1 mm, usually from 0.01 mm to 0.1 mm. In the case of treatment of arterial sites, the scoring can not only deliver the drug to regions within the thrombus or plaque, it can further score the vascular wall and deliver the drug into the intimal and subintimal layers surrounding the blood vessel.

In addition to treatment of blood vessels, the methods and systems of the present invention can be used to treat a variety of other body lumens, including vein grafts and synthetic grafts, as well as lumens of the respiratory, urinary, reproductive and digestive systems, and the like.

The benefits of drug delivery using scoring or cutting device include rapid (short term) release to intimal and subintimal areas rather than sustained delivery over few days or weeks with DES (constant concentration over time). The combination of scoring the lesion to open diffusion channels and delivering therapeutic agent directly to the diffusion channels increases the efficacy of the system.

The methods and systems of the present invention are particularly useful for delivering drugs which are hydrophobic and lipophilic. The hydrophobic nature of some drugs (e.g. paclitaxel and sirulimus) and the fact that those drugs are lipophilic (i.e. high affinity to liposome) help retain the drug for longer time in the lesion and minimize the loss of rug during the time of delivery due to dissolution in the blood.

Given the above, the characteristics of the polymer matrix may very different from stents. Ideally the drug diffuses over a short period of time (few seconds to several minutes in the case of the circulation system) to the lesion not to diffuse over time (days or weeks). Many different polymers can be used including polymers that will dissolve in blood within the interaction time and those that will not be dissolve but will release drug.

The scoring element(s) are typically positioned using an intravascular or other intraluminal catheter which carries one or more scoring elements at or near its distal end. In the case of blood vessels, the catheter is typically introduced over a guidewire in a conventional manner, e.g., through the femoral artery to reach the coronary arteries or through sheath in case of peripheral arteries.

The scoring element(s) may be advanced to score a plaque in a body lumen by radially advancing the scoring elements into the lesion and the luminal wall. Typically, such radial expansion is achieved using an expandable shell, such as an inflatable balloon carried by the catheter. Alternatively, the radial expansion can be achieved using self-expanding materials such as nitinol or expandable geometries using other materials (such as stainless steel). Scoring elements may have any of the geometries previously used in scoring devices, including the linear geometries of the scoring elements employed in the IVT devices, as described above. Preferably, however, the scoring elements will comprise one or more resilient elements having helical geometries, as taught by co-pending patent application Ser. No. 10/631, 499, filed on Jul. 30, 2003; Ser. No. 10/810,330, filed on Mar. 25, 2004; and Ser. No. 10/917,917, filed on Aug. 13, 2004, assigned to the assignee of the present application, the full disclosures of which are incorporated herein by reference.

Regardless of the geometry of the scoring elements, radial advancement will usually comprise expanding an expandable shell, such as an inflatable balloon, which carries at least one scoring element. In this way, the outward edge(s) of the scoring element can engage and penetrate the luminal wall and/or the occlusive or other material which covers at least a portion of the luminal wall. Alternatively, the radial expansion can be achieved using self-expanding materials such as nickel titanium alloys or expandable geometries using other materials (such as stainless steel). Scoring element can be expanded by other means by using temperature controlled structured (i.e. made of heat memory alloys) or mechanical means such as internal sliders with an increased diameter.

The methods, catheters, and systems of the present invention can be utilized to deliver a wide variety of active substances, including drugs useful for treating a wide variety of luminal diseases and conditions. The methods and apparatus of the present invention are particularly useful for delivering a wide variety of therapeutic and pharmaceutical agents, referred to collectively herein as active substances, particularly those suitable for treating vascular and other luminal conditions, including:

(1) antiproliferative and antimitotic agents such as natural products such as vinca alkaloids (i.e. vinblastine, vincristine, and vinorelbine), paclitaxel, epidipodophyllotoxins (i.e. etoposide, teniposide), antibiotics (dactinomycin, actinomycin D, daunorubicin, doxoruhicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine);

(2) antiplatelet agents such as G(GP) II.b/III.a inhibitors and vitronectin receptor antagonists;

(3) alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC);

(4) antiproliferative and antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine));

(5) platinum coordination complexes such as cisplatin, carboplatin, procarbazine, hydroxyurea, mitotane, and aminoglutethimide;

(6) hormones (e.g. estrogen);

(7) anticoagulants (heparin, synthetic heparin salts and other inhibitors of thrombin);

(8) fibrinolytic agents (such as tissue plasminogen activator, streptokinase and urokinase), aspirin, dipyridamole, ticlopidine, clopidogrel, abciximab;

(9) antimigratory agents;

(10) antisecretory agents (breveldin);

(11) anti-inflammatory agents, such as adrenocortical steroids (cortisol, cortisone, fludrocortisone, prednisone, prednisolone, 6α methylprednisolone, triamcinolone, betamethasone, and dexamethasone), non-steroidal agents (salicylic acid derivatives i.e. aspirin; para-aminophenol derivatives i.e. acetaminophen;

(12) indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate);

(13) immunosuppressive agents such as cyclosporine, tacrolimus (FK-506), sirolimus (rapamycin), azathioprine, mycophenolate, mofetil;

(14) angiogenic agents such as vascular endothelial growth factor (VEGF), fibroblast growth factor (FGF);

(15) angiotensin receptor blockers;

(16) nitric oxide donors;

(17) anti-sense oligionucleotides and combinations thereof;

(18) cell cycle inhibitors, mTOR inhibitors, and growth factor receptor signal transduction kinase inhibitors;

(19) retenoids;

(20) cyclin/CDK inhibitors;

(21) HMG co-enzyme reductase inhibitors (statins); and

(22) protease inhibitors.

The present invention further comprises catheters for delivering active substances to body lumens. Catheters of the present invention comprise a catheter body having a proximal end and a distal end and a scoring element disposed near the distal end. The scoring element comprises an active substance that is delivered to a luminal wall scored or cut by the scoring element. The active substance may be provided on or within the scoring element in a variety of ways. For example, the active substance may be coated over at least a portion of an exposed surface of the scoring element, typically by dipping, spraying, painting, plasma deposition, electroplating, centrifuge systems or the like. More typically, however, the active substance may be incorporated in a polymeric carrier. Suitable polymeric carriers may be resorbable, such as those comprising polylactic acids (PLA), polyglycolic acids (PLO), collagens, and the like. Alternatively, the polymeric carrier may be a porous but non-resorbable material such as porous silicon or polyethylene. Hydrogels such as Poly Ethylene Oxide (PEO) may be used and release the drug through swelling and erosion. Degradable polymers which include polyhydroxyalkanoate can be used as well. The polymer can coat the scoring element struts or alternatively can create a film between at least some of the scoring element struts or any combination of the above.

Coatings may comprise a polymer matrix such as vinylpyrrolidone-vinyl acetate, styrene acrylic polymer, ethylene acrylic acid copolymer, carboxyl function acrylic polymer, hydroxyl function acrylic polymer, and acrylic dispersion polymer, among others. In some cases it is desirable to use a coherent bond coat (i.e. epoxies, acetals, acrylics, ethylene copolymers, or other suitable groups). Coatings may also comprise poly(glycol methacrylate), poly(methyl methacrylate), poly(ethyl methacrylate), poly(butyl methacrylate), poly(sulfanato ethyl methacrylate), polyethylene-co-vinyl acetate), poly(ethyl acrylate), polyurethane-acrylate), polyacrylamide-co-ethyl methacrylate), poly(divinyl benzene), poly(triethylene glycol-co-divinyl ether), poly(tri-methylol propane triacrylate), poly(pentaerythritol tetraacrylate), poly(bisphenol A ethoxylate diacrylate), poly(allyl ether), poly(diallyl maleate), poly(vinylidene fluoride), poly(triallyl isocyanurate), poly vinyl alcohol, ethylene vinyl alcohol copolymer, or alike. The drug may also be carried on the surface of the scoring element using an oxide layer or porous oxide layer. Alternatively the scoring element may be coated by drug without any polymer or carrying matrix of any kind.

As an alternative to coating, the active substances, either with or without a polymer carrier, may be incorporated into apertures, such as holes, grooves, or wells formed in the scoring element. The apertures may be distributed over the entire surface of the scoring element, or may be provided over only portions thereof. The active substances will thus be released from the apertures when the scoring elements are engaged against the luminal wall.

Scoring elements may have any conventional geometry, generally as described above, including linear, helical, or other geometries. In the exemplary embodiments, the scoring elements will be formed as at least a portion of a resilient cage which surrounds an expandable shell carried by the treatment catheter. The resilient cage will have a structure which expands with shell expansion and collapses over the shell, e.g., helping to deflate a balloon which carries the cage.

BRIEF DESCRIPTION OF THE DRAWINGS

FIG. 3 is a schematic illustration of an expanded angioplasty balloon carrying a helical scoring structure in accordance with embodiments of the invention.

FIG. 6 illustrates a scoring structure comprising alternating C-shaped scoring elements between a pair of end collars.

FIG. 7 illustrates the C-shaped scoring elements of the embodiment of FIG. 6 shown in a rolled-out configuration.

FIG. 8 is a view of one of the C-shaped scoring elements taken along line 8-8 of FIG. 6.

FIG. 9 illustrates an alternative double C-shaped scoring element which could be utilized on a scoring structure similar to that illustrated in FIG. 6.

FIG. 10 illustrates an alternative embodiment of a helical scoring structure comprising serpentine and zigzag structures for mounting onto a balloon catheter.

FIG. 11 illustrates a first of the serpentine mounting elements of the scoring structure of FIG. 10.

FIG. 12 illustrates a second of the serpentine mounting elements of the scoring structure of FIG. 10.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Embodiments of the present invention relate to device for revascularization of stenotic vessels and specifically to a balloon catheter having external elements. The dilatation device comprises a conventional dilatation balloon such as a polymeric balloon and a spiral, or external elements with other configurations mounted on the balloon catheter. The apparatus comprises one or more scoring elements which are coated or otherwise loaded with an active substance to be released into a blood vessel wall or stenotic region in accordance with the principles of the present invention. The invention will also find use in treating other body lumens, such as vein and synthetic grafts, as well as lumens of the respiratory, urinary, reproductive and digestive systems, and the like, for other conditions such as lesions or tumors or some types of cancer or other local disorders.

Figure 1:
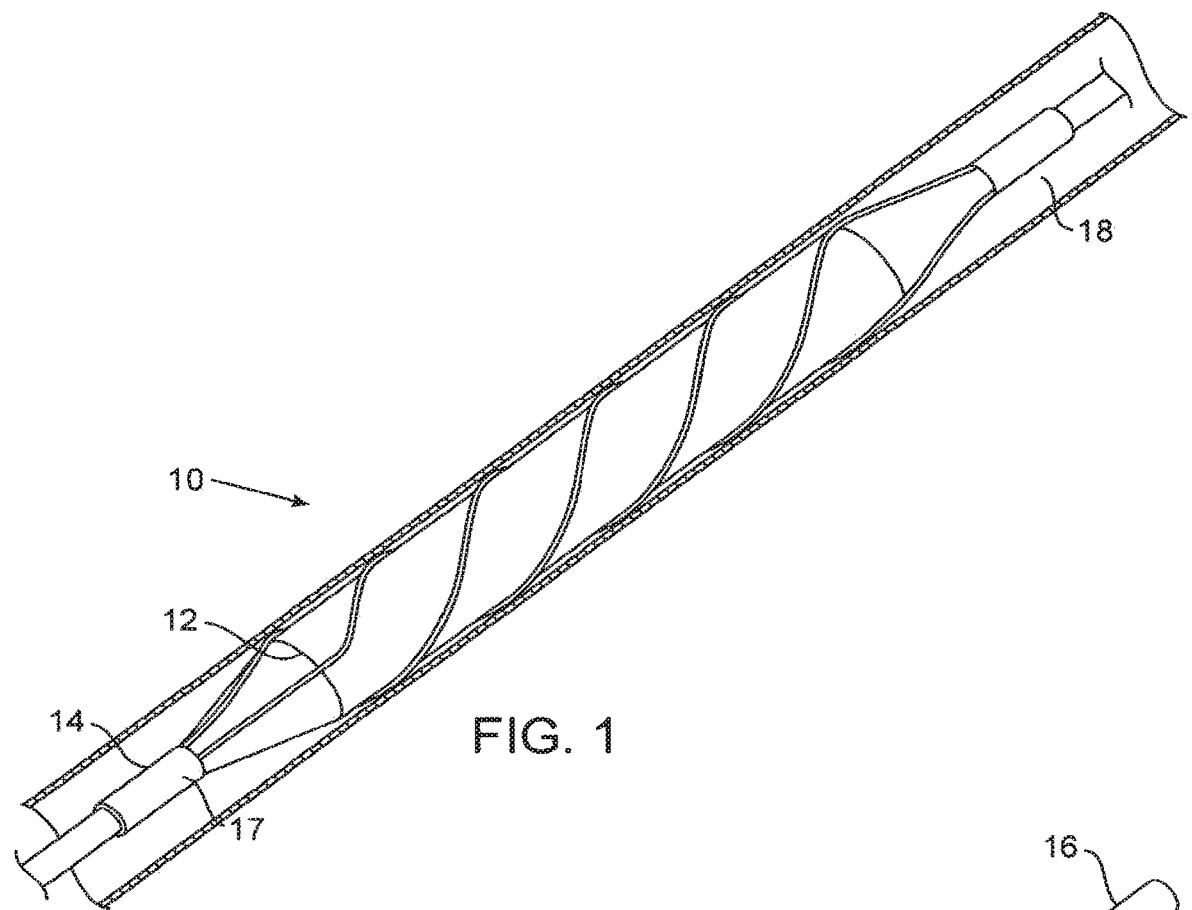
FIGS. 1, 1A, 1B and 1C are schematic illustrations of the balloon scoring structure embodiment in accordance with an embodiment of the invention.
Figure 1A:
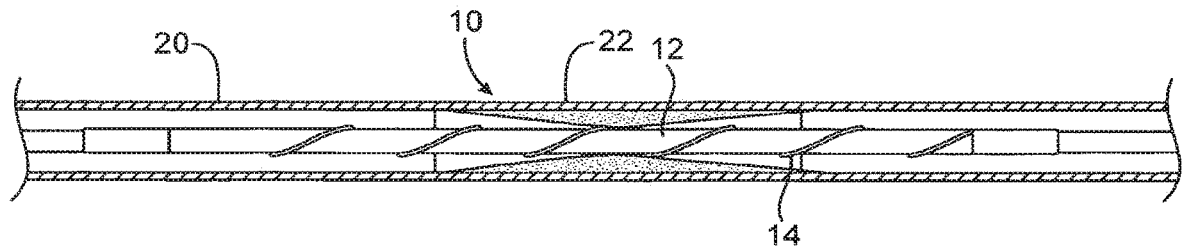
Figure 1B:
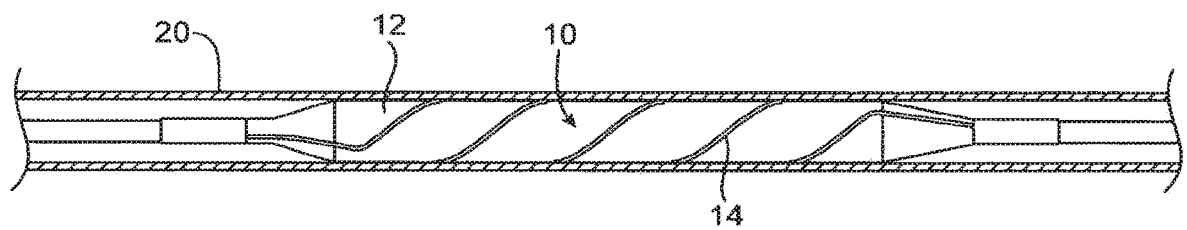

Reference is now made to FIGS. 1, 1A and 1B, which are schematic illustrations of a dilatation device 10 in accordance with embodiments of the invention. The devices will first be described without incorporation of a drug or other active substance. Particular methods and structure for incorporating such drugs and substances are described in detail below. The dilatation device 10 includes a dilatation balloon 12, which may be any conventional angioplasty balloon such as commonly used by interventional cardiologists or radiologists, and a helical or spiral unit 14 mounted over or attached to dilatation balloon 12. The compliance of the balloon and the scoring element(s) should be chosen to assure uniform expansion of the balloon substantially free from "dog-boning" as the combined structure expands within a lesion. If a compliant or a semi-compliant balloon is used and the compliance of the scoring element was not matched to comply with the properties of the balloon, the expansion of the balloon-scoring element system will not be uniform. This non-uniformity may impair the efficacy of the scoring catheter and, in some cases, may result in poor performance. For example, under given pressure, certain parts of the balloon will be able to expand while other parts will be constrained by excessive resistance of the scoring elements.

Helical unit 14 typically made of nitinol. Helical unit 14 may be made of other metals such stainless steel, cobalt-chromium alloy, titanium, and the like. Alternatively, spiral unit 14 may be a polymeric spiral, or made of another elastic material. Helical unit 14 may be attached at its proximal and distal ends to the proximal end 17 and distal end 18 of dilatation balloon 12. Alternatively, spiral unit 14 may be attached to the distal end and/or the proximal end of dilatation balloon 12 by collar-like attachment elements 15 and 16. Spring or other compliant elements may be alternatively or additionally provided as part of the attachment elements to accommodate shortening of the helical unit as it is expanded.

Dilatation device 10 is inserted into the vascular system, for example, using a conventional catheter procedure, to a region of stenotic material 22 of blood vessel 20. (The term "stenotic" is used herein to refer to the vascular lesion, e.g., the narrowed portion of the vessel that the balloon is meant to open.) At the stenotic area, the dilatation balloon 12 is inflated, for example, by liquid flow into the balloon. Helical unit 14 widens on the inflated dilatation balloon 12. On inflation, the dilatation balloon 12 together with the helical unit 14 is pressed against the walls of blood vessel 20 as shown in FIG. 1B.

Figure 1C:
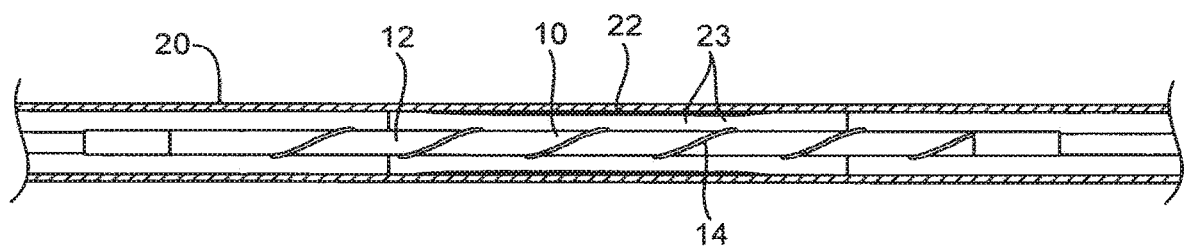

Reference is now made to FIG. 1C, illustrating blood vessel 20 after the deflation of dilatation balloon 12. Helical unit 14 narrows when deflating the dilatation balloon 12, thus the dilatation device 10 is narrowed and may be readily retrieved from blood vessel 20.

The deflation profile of the balloon 10 is low and mainly circular. The stenotic material 22 in blood vessel 20 is pressed against blood vessel 20 walls to widen the available lumen and enhance blood flow. The pressing of helical unit 14 against the walls of blood vessel 20 causes scoring 23 in the stenotic area.

Reference is now made to FIG. 3 that shows a scoring structure in the form of a single wire 24 wrapped around a dilatation balloon 12 in a helical configuration.

In other embodiments, the scoring structure of the present invention can have a non-helical configuration. Any design of scoring structure that can accommodate an increase in the diameter of the balloon 12 upon inflation, and return to its configuration when the balloon is deflated, is an appropriate design useful in the invention. At least a portion of the scoring elements will not be parallel to the longitudinal axis of the balloon catheter to enhance flexibility and improve scoring.

Referring again to FIGS. 1A-1C, helical unit 14 is pushed outwardly by the inflation of the balloon 12, and is stretched by the inflation of the balloon. When the balloon is deflated, helical unit 14 assists in the deflation by its elastic recoil. This active deflation is faster and also leads to a low profile of the deflated balloon. The balloon 12 is disposed within the helical unit 14, which returns to its pre-inflated shape and forces the balloon to gain a low radial profile.

In another embodiment of the invention, dilatation device 10 may carry a stent. The stent can be crimped over the helical unit 14, In this way, the helical unit 14 can push the stent against hard areas of the lesion, enabling proper positioning of the stent against the vessel wall, even in hard-calcified lesions without pre-dilation.

Figure 2:
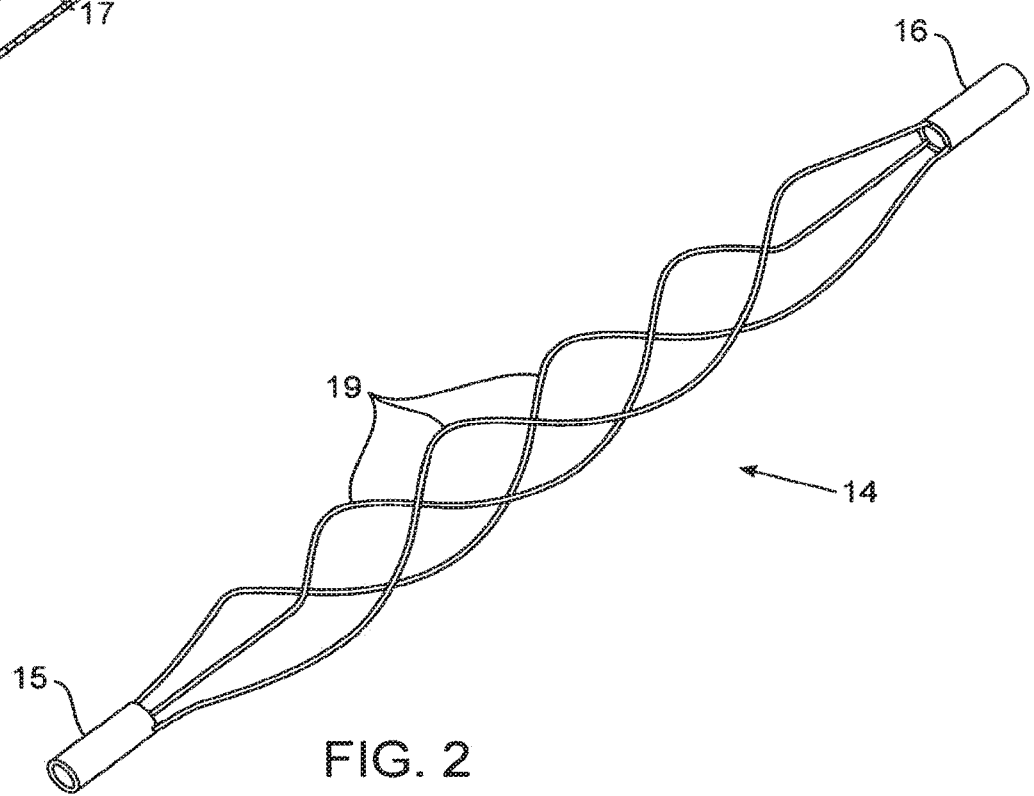
FIG. 2 is a schematic illustration of an exemplary helical scoring structure embodiment in accordance with embodiments of the invention.

Reference is now made to FIG. 2, illustrating the helical unit 14 in accordance with embodiments of the invention. Helical unit 14 is typically made of nitinol, Helical unit 14 includes three wires 19 that are attached to collars 15 and 16 at the proximal end and distal end, respectively. Alternatively the scoring structure may be formed as a metallic cage, which can be made from a slotted tube, or polymeric cage or polymeric external elements. Alternatively the scoring structure may comprise wires of other elements attached directly to the balloon material or close to the balloon ends.

Wires 19 (FIG. 2) are attached between collars 14 and 15. The diameter of the wires is typically in the range of 0.05 mm to 0.5 mm. Alternatively, a cage (for example a metallic cage made of a slotted tube) can be used in several configurations that allow local stress concentrations. The size and shape of the cross section of the cage elements or the cross section of the wires can vary. The cross section can be a circle, rectangle, triangle, or other shape.

In alternative embodiments, the wires 19 may comprise short segments that are attached to the balloon 12, In further alternative embodiments of the invention, the helical unit 14 may be glued, thermally bonded, fused or mechanically attached at one or both ends to dilatation balloon 12.

In yet another embodiment, a scoring structure may comprise wires that are attached to the dilatation balloon 12 in helical configuration or other configuration. The wires may be thermally attached to the balloon 12, glued, mechanically attached, or the like.

In still another embodiment, a scoring structure comprises wire or cage elements that are not parallel to the longitudinal axis of the balloon 12 so that the combination of the scoring structure 19 and the balloon 12 remains flexible.

In additional embodiments, the combination of dilatation balloon 12 and scoring structure scores the lesion and provides better vessel preparation for drug eluting stents by allowing better positioning of the stent against the vessel wall and diffusion of the drug through the scores in the lesion.

In these embodiments, the balloon can be used as a platform to carry drugs to the lesion where scoring of the lesion can enhance delivery of the drug to the vessel wall.

In these embodiments, the balloon can be used for a local drug delivery by embedding drug capsules, drug containing polymer, and the like, through the stenotic material and into the vessel wall.

From the above, it can be seen that the invention comprises catheters and scoring structures, where the scoring structures are positioned over the balloons or other expandable shells of the catheter. The scoring structures may be attached directly to the balloons or other shells, in some cases being embedded in the balloon material, but will more usually be formed as separate cage structures which are positioned over the balloon and attached to the catheter through attachment elements on either side of the balloon. The expandable cages may be formed using conventional medical device fabrication techniques, such as those used for fabricating stents, such as laser cutting of hypotube and other tubular structures, EDM forming of hypotubes and tubes, welding of wires and other components and the like.

Typically, such expandable shell structures will comprise the attachment elements and an intermediate scoring section between the attachment elements. As illustrated in the embodiments above, the attachment elements may be simple cylindrical or tube structures which circumscribe the catheter body on either side of the balloon or other expandable shell. The simple tube structures may float over the catheter body, i.e., be unattached, or may be fixed to the catheter body. A number of alternative embodiments for the attachment elements will be described in connections with the embodiments below.

The intermediate scoring sections may also have a variety of configurations where at least some of the scoring elements will typically be disposed in a non-axial configuration, i.e., in a direction which is not parallel to the axial direction of the expandable cage. A preferred configuration for the intermediate scoring section comprises one or more helical elements, generally as illustrated in the prior embodiments. Other exemplary configurations are set forth in the embodiments described below.

Figure 4:
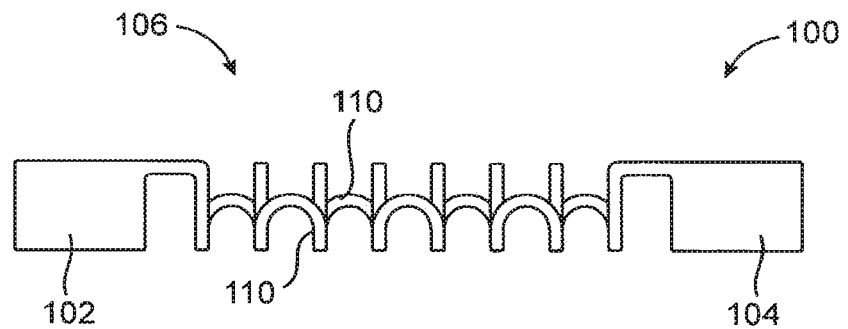
FIG. 4 illustrates a scoring structure comprising an alternating serpentine pattern of intermediate scoring elements between a pair of end collars.
Figure 5:
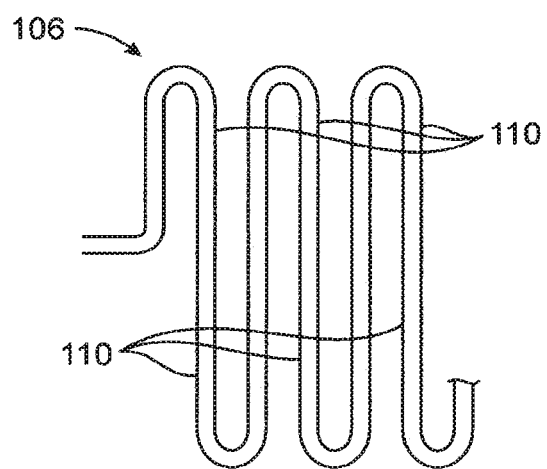
FIG. 5 illustrates the serpentine scoring elements of the embodiment of FIG. 4 showed in a rolled-out configuration.

Referring now in particular to FIGS. 4 and 5, an expandable scoring cage 100 comprises first and second attachment elements 102 and 104, respectively, and an intermediate scoring section 106 comprising a plurality of curved serpentine members 110. The serpentine members 110 extend circumferentially in opposite directions in an alternating manner. This can be understood by observing a "rolled-out" view of the serpentine elements as illustrated in FIG. 5. A second alternative scoring cage structure 120 is illustrated in FIGS. 6-8. The scoring cage 120 comprises first and second attachment elements 122 and 124 joined by a spine 126. Plurality of C-shaped scoring elements 128 and 130 are attached to the spine and extend in opposite circumferential directions. The shape of the element can be observed in FIG. 8. The opposite directions may be observed in the rolled-out view of FIG. 7.

It will be appreciated that a variety of different circumferential structures may be used in place of the C-shaped structures of FIGS. 6-8, For example, a pair of opposed C-shaped partial ring structures may be utilized, as illustrated in FIG. 9. The C-shaped structures of FIG. 6 or the double C-shaped structures of FIG. 9 can also be extended so that they wrap around a balloon more than one time, either over or under the spine structure 126.

The expandable cage structures 100 and 120 will each be mounted over a dilatation balloon, such as the balloon of FIGS. 1-3, with the attachment elements secured to the catheter body on either side of the dilatation balloon. The tube or cylindrical attachment elements 102, 104, 122, and 124 may simply float over the catheter body. In other embodiments, however, it may be desirable to use an adhesive or other means for affixing either one or both of the attachment elements to the catheter body. Having at least one floating attachment element, however, is often desirable since it can accommodate shortening of the intermediate scoring section as that section radially expands. In other cases, however, the individual scoring elements may possess sufficient elasticity to accommodate such shortening. For example, nitinol and other shape memory alloys possess significant stretchability, typically on the order of 8% which in some instances will be sufficient to accommodate any tension applied on the intermediate scoring section by radial expansion of the balloon.

Referring now to FIGS. 10-12, alternative attachment elements are shown on an embodiment of an expandable scoring cage 140 comprising three helical scoring elements 142 which make up the intermediate scoring section. A first attachment element 146 comprises a single serpentine ring, as best illustrated in FIG. 11 while a second attachment element 148 comprises a pair of tandem serpentine rings 150 and 152, as best illustrated in FIG. 12. The use of such serpentine attachment structures is beneficial since it permits crimping of either or both of the structures onto the catheter body in order to fix either or both ends of the structure thereto. Usually, the single serpentine attachment structure 48 will be affixed to the catheter body while the double serpentine structure will be left free to allow movement of that end of the scoring cage to accommodate radial expansion of the underlying balloon.

Figure 13:
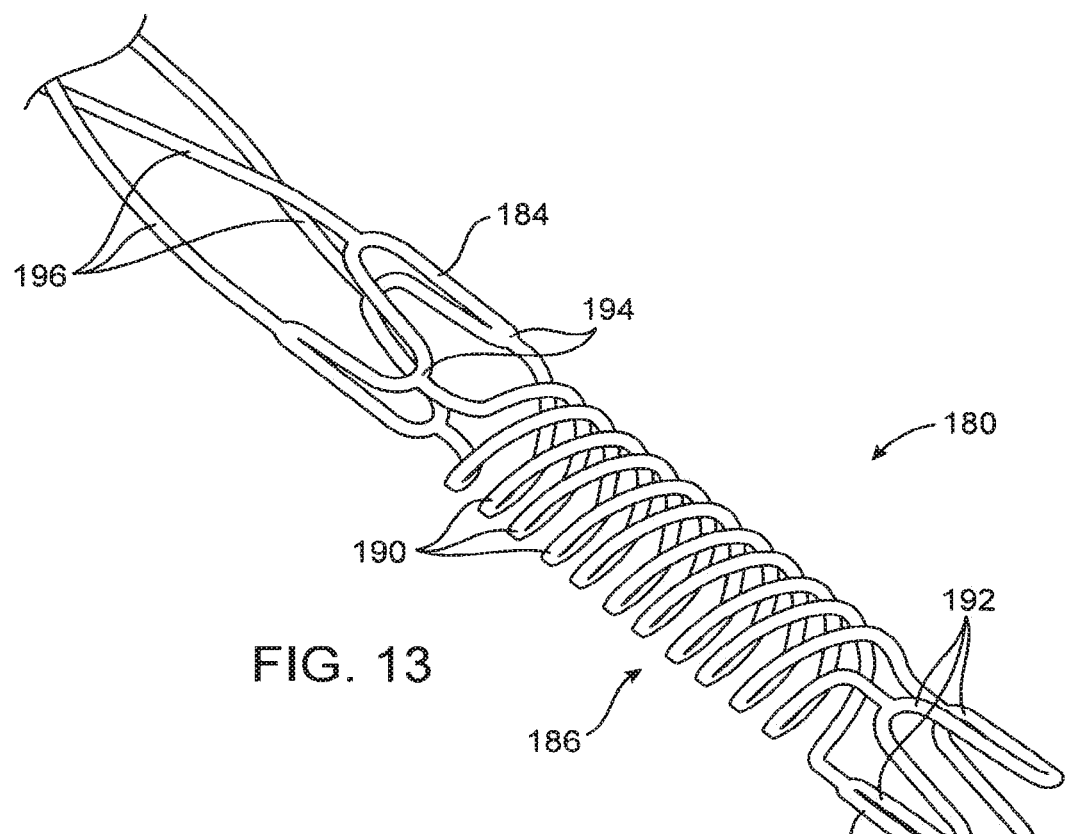
FIG. 13 illustrates an alternative mounting structure for a helical or other scoring structure.
Figure 14:
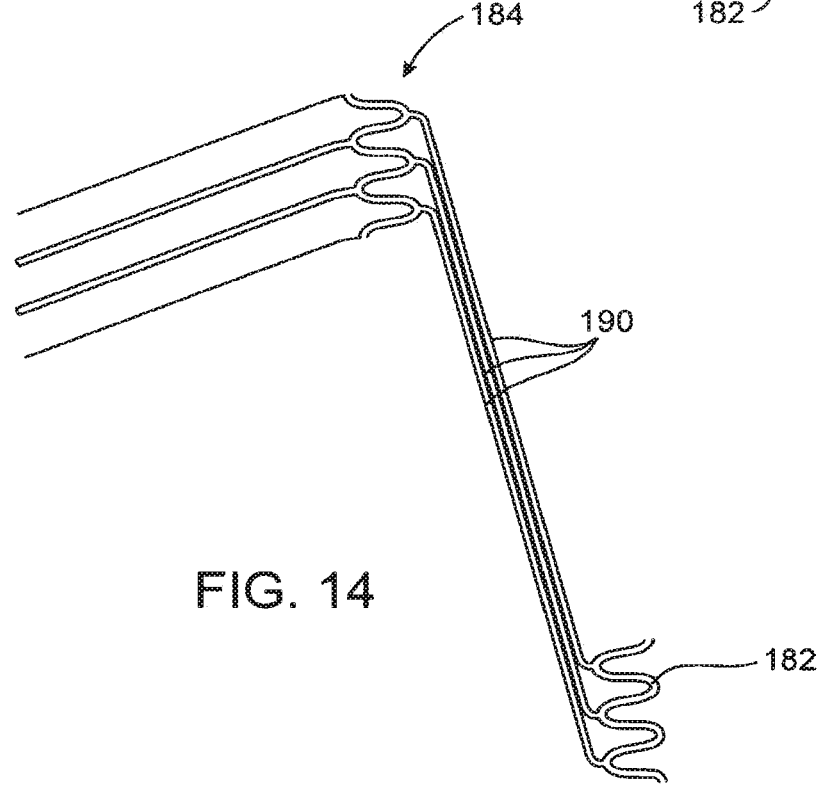
FIG. 14 illustrates the mounting structure of FIG. 13 shown in a rolled-out configuration.

Referring now to FIGS. 13 and 14, a further alternative embodiment of an attachment element useful in the scoring cages of the present invention is illustrated. Attachment element 180 includes a pair of serpentine rings 182 and 184, generally as shown in FIG. 12, in combination with a coil spring structure 186 located between said rings 182 and 184. The coil spring structure 186 includes three nested coil springs 190, each joining one of the bend structures 192 and 194 on the serpentine rings 182 and 184, respectively. The structure of the spring structure and adjacent serpentine rings can be understood with reference to the rolled-out configuration shown in FIG. 14.

The attachment structure 180 is advantageous since it permits a fixed attachment of the outermost ring 182 to the underlying catheter body while the inner ring 184 remains floating and expansion and contraction of the intermediate scoring section, comprising helical elements 196, is accommodated by the coil spring structure 186. Since the scoring cage is fixed to the catheter, any risk of loss or slippage from the balloon is reduced while sufficient compliance is provided to easily accommodate radial expansion of the intermediate scoring section. By attaching the structures 180 at least one, and preferably both ends of the scoring cage, the risk of interference with a stent is reduced.

In some embodiments, collars, such as those shown in FIGS. 1 and 2, or attachment elements, such as those shown in FIGS. 10-12, may comprise a flexible material that allows the collar or attachment element to expand while being mounted over the balloon catheter and then be collapsed to the diameter of the catheter. The expandability of the collars and/or attachment elements may be achieved by a compliant memory material such as nitinol or a polymer, or by use of a flexible serpentine design as shown in FIGS. 10-12. Where collars are used, the collar may be shaped or have a slit down the circumference (not shown) so that the collar may be expanded during mounting over the balloon. Alternatively, the collar may be oversized to accommodate the balloon diameter mounting, and then crimped down to secure the secure the scoring structure to the catheter body.

Figure 15:
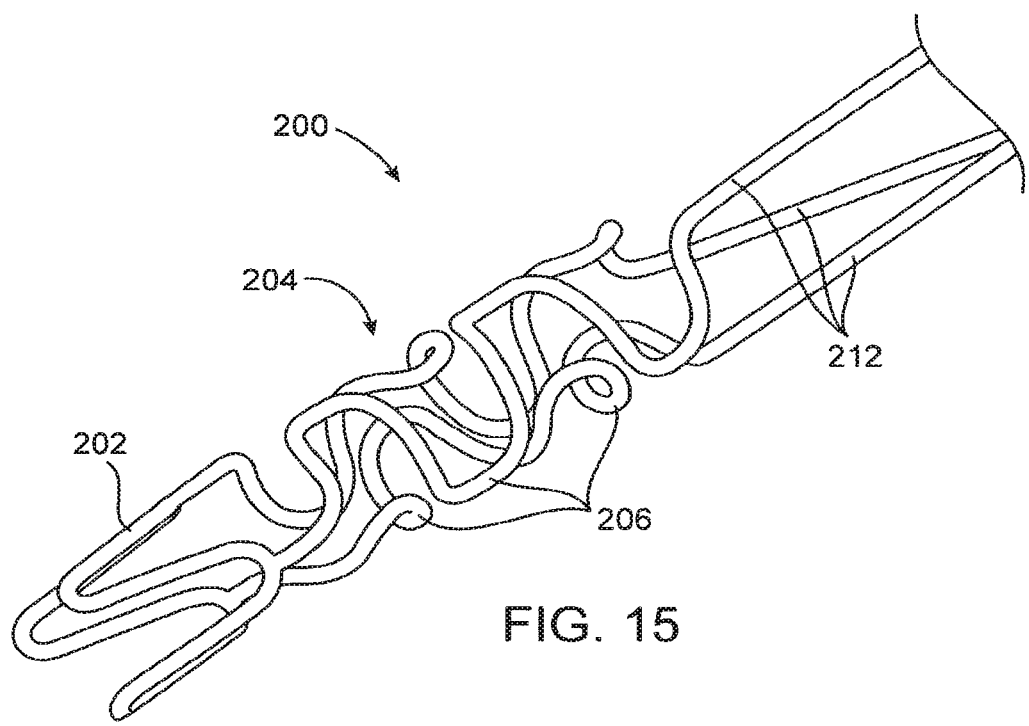
FIG. 15 shows yet another embodiment of a mounting element for the scoring structures of the present invention.
Figure 16:
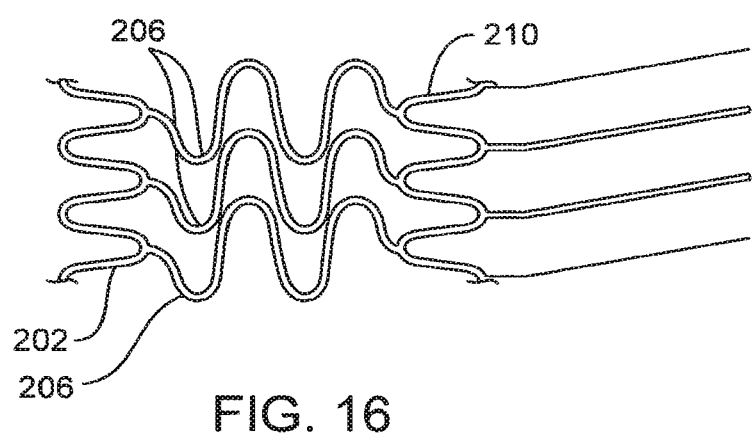
FIG. 16 illustrates the mounting structure of FIG. 15 shown in a rolled-out configuration.

Yet another embodiment of the attachment element of the present invention includes an axial spring as shown in FIGS. 15 and 16. The attachment element 200 includes a terminal serpentine ring 202 and an intermediate spring structure 204 including a number of axial serpentine spring elements 206. The nature of the serpentine ring elements 206 can be observed in the rolled-out configuration of FIG. 16. Optionally, a second serpentine ring 210 may be provided between the attachment structure 200 and the helical scoring elements of the intermediate scoring section 212.

The embodiments of FIGS. 13-16 comprise spring-like elements 186 and 204 to accommodate axial shortening of the scoring structure upon radial expansion. It will be appreciated that other metal and non-metal axially extensible structures could also be used in such attachment structures. For example, elastic polymeric tubes could be attached at one end to the scoring structures and at another end to the catheter body (or to a ring, collar or other structure which in turn is fixed to the catheter body).

Figure 17A:
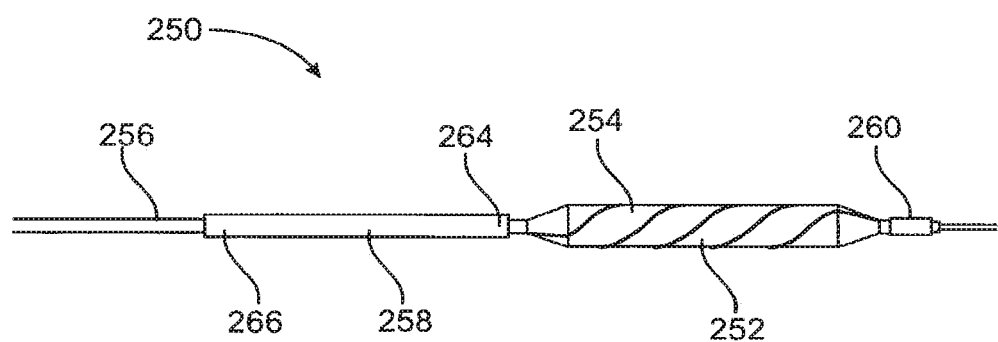
FIG. 17a illustrates yet another alternative embodiment of a catheter constructed in accordance with the principles of the present invention, where an attachment structure is disposed between the scoring structure and the catheter body.
Figure 17B:
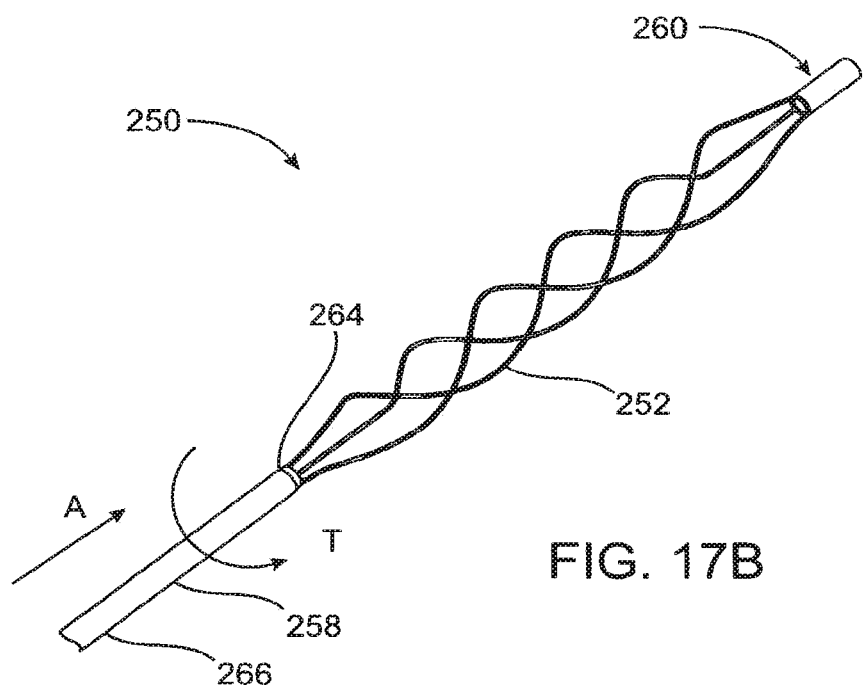
FIG. 17b illustrates the structure of FIG. 17a shown without the balloon.

Referring now to FIGS. 17a and 17b, a further embodiment of an angioplasty catheter 250 having an axially distensible attachment structure 258 is illustrated. External structure 252 is held over expandable dilatation balloon 254 and is fixed at one end to the distal end 260 of catheter body 256, The external structure may comprise any structure typically used for removal of plaque/thrombus from a vessel wall such as a scoring structure, cutting structure or crushing structure. The proximal end 262 of external structure 252 is connected to the distal end 264 of attachment structure 258. The proximal end 266 of attachment structure 258 is fixed to the catheter body 256. As described below, the attachment structure 258 may be configured to reduce forces applied on the external structure 252 and the catheter body 256 during expansion and contraction of balloon 254.

In a preferred embodiment, attachment structure 258 comprises a cylindrical over-tube, or compliance tube, made of an elastic material. Over-tube 258 generally has an inner diameter that is slightly greater than the outer diameter of the catheter body 256. Because only a small section of the proximal end of the attachment structure 258 is fixed to the catheter body, the distal end 264 attached to external structure 252 is free floating, and is free to slide axially and rotationally with respect to catheter body 256. Attachment structure 252 may be fixed, for example by adhesion, directly to the to catheter body 256 and external structure 252, or to a collar or other intermediate attachment means.

As balloon 254 is expanded, external structure 252 expands in circumference and contracts axially along the catheter body 256, creating axial force A on attachment structure 258. Attachment structure 258, fixed to the catheter at its end 266, axially stretches to accommodate the axial movement of the external structure 252. External structure 252 also tends to rotate about the catheter body 256, causing a torsional force T. The distal end 264 of attachment structure 258 rotates through the full range of motion of scoring structure 252 to accommodate torsional force T, while proximal end 266 remains stationary with respect to catheter body 256.

The configuration illustrated in FIGS. 17a and 17b allows the compliance of the expandable system to be controlled. Generally, where one end of the scoring structure is free, the compliance of the expandable system will be a combination of the compliance of the balloon and the scoring structure. However, because the ends of the expandable system shown in FIG. 17 are fixed at distal end 260 and proximal end 266, the attachment structure controls the compliance of the expandable system.

The compliance of the system may be varied by any combination of material selection, wall thickness, or length of the over-tube 258. Over-tube 258 may comprise any elastomer, such as elastic polymer like Nylon, Pebax, or PET. Typically, compliance tube 258 is formed from extruded tubing, but is may also comprise braided polymeric or metallic fibers, or wire mesh. A high memory metal such as nitinol or stainless steel may also be used. Where the compliance tube comprises an extruded polymeric tube, the wall thickness can vary in the ranges set forth above, and the length of the tube can range from 1 cm to 10 cm. For the same material, the thinner-walled and longer the tube, the more compliant the system.

Figure 18A:
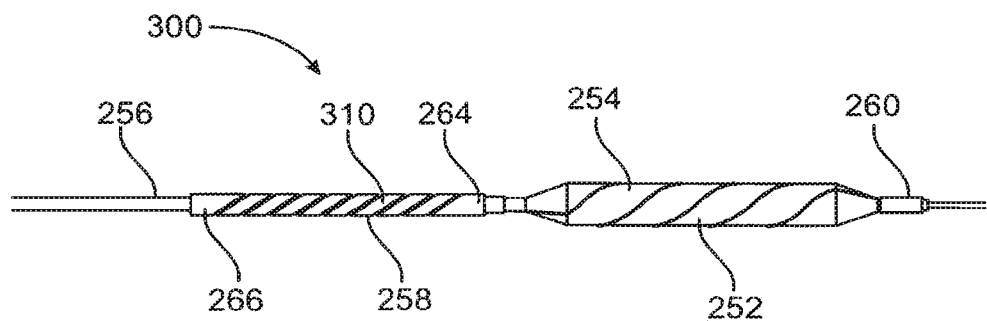
FIGS. 18a-c illustrate a catheter constructed in accordance with the principles of the present invention having an attachment structure with various patterned perforations.
Figure 18B:
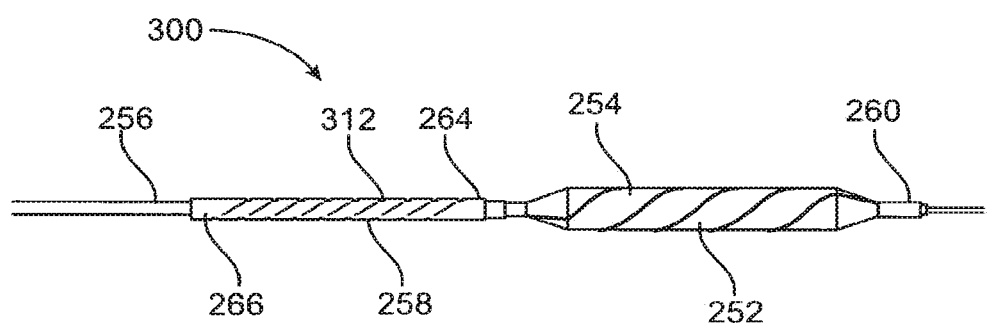
Figure 18C:
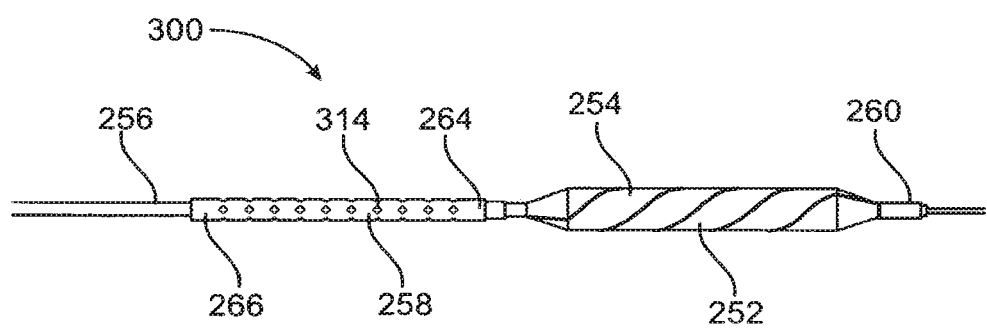

Referring to FIGS. 18a-c, the compliance of a angioplasty catheter 300 may also be varied by creating one or more perforations in compliance tube 258. The perforations may comprise one or more slots in the circumference of the tubing. The slots may comprise one continuous slot spiraling across the length of compliance tube 258, or may be a number of slots aligned in any number of patterns, such as helical 312, or radial 314. The slots may also be any number of shapes, such as circular or rectangular, and may have a discreet length or be contiguous across the surface of the compliance tube.

Figure 19:
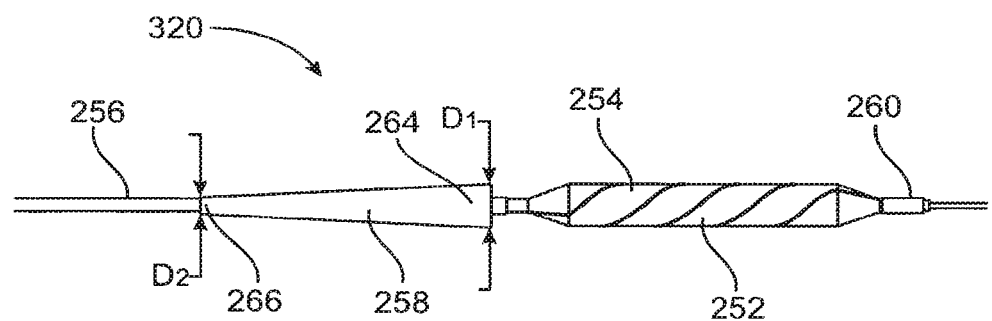
FIG. 19 illustrates another embodiment of a catheter constructed in accordance with the principles of the present invention having a tapered attachment structure.

Referring to FIG. 19, the outside diameter of compliance tube 258 may be tapered to facilitate delivery and retrieval of the scoring catheter 320 from the treatment site within the lumen. Generally, the outer diameter will be larger at the distal end 264 of the compliance tube 258 and smaller at the proximal end 266 of the compliance tube. The outside diameter $D_1$ at the distal end will vary depending on the profile of the scoring structure and balloon when collapsed but typically range from 0.004 in, to 0.01 in. larger than the outside diameter $D_2$ at the proximal end. The outside diameter $D_2$ at the proximal end is generally as close as possible to the outside diameter of the catheter body to create a smooth transition between the compliance tube and the catheter. As an example, for a catheter body having an outside diameter of 0.033 in., outside diameter $D_1$ at the distal end may be 0.042 in. with an inner diameter of 0.038 in., the inner diameter providing clearance between the catheter body so that the distal end of the compliance tube can move relative to the catheter body. Correspondingly, the outside diameter $D_2$ at the proximal end may taper down to 0.0345 in., with an inner diameter of 0.034 in. to closely match the catheter body having outside diameter with enough clearance to be bonded to the catheter body by an adhesive.

The taper may run across the whole length of the compliance tube, or alternatively be only tapered at a section of the length of the compliance tube. The tapered compliance tube 258 smoothes the transition between the scoring structure and catheter body, and minimizes the likelihood of the outer tube or scoring structure snagging or catching on a portion of the luminal wall during delivery or retrieval of the catheter.

Figure 20:
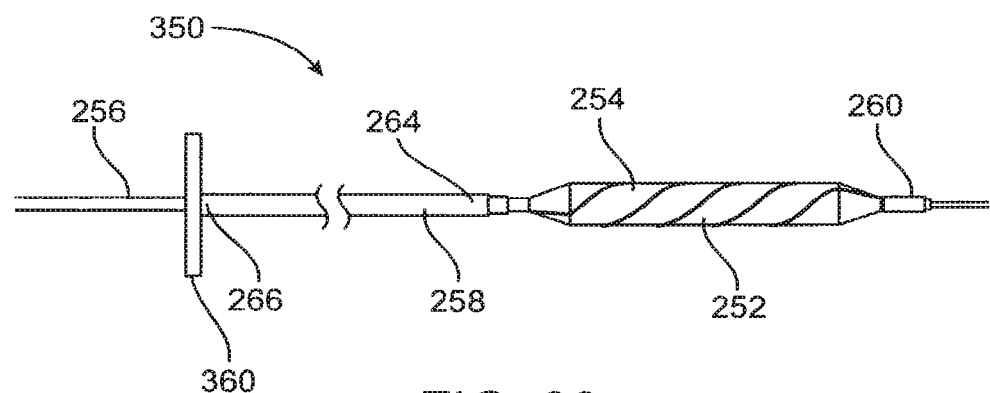
FIG. 20 illustrates yet another alternative embodiment of a catheter constructed in accordance with the principles of the present invention, where an attachment structure is connected to a manipulator.

Now referring to FIG. 20, an alternative embodiment of a scoring catheter 350 is shown having a manipulator 360. The attachment structure 258 is connected at its distal end 264 to the scoring structure 252. Instead of being secured directly to the catheter body 256, the proximal end 266 is attached to manipulator 360. Typically, the manipulator 360 is positioned at the proximal end of the catheter body 256 and the attachment structure 258 extends from the scoring structure across the length of the catheter body. Like the above embodiments, the attachment structure is capable of axially and rotationally extending to accommodate foreshortening of the scoring structure as the shell is expanded.

In some embodiments, the compliance of the scoring structure 252 and balloon 254 is controlled by actuating the manipulator during expansion or contraction of the radially expandable shell. In one aspect, the attachment structure 258 may be axially advanced with respect to the catheter body 256 as the balloon is being inflated or deflated. For example, the attachment structure 258 may be pulled away from the distal end of the catheter body 256 while the balloon 254 is being expanded to constrain the compliance of balloon. The attachment structure 258 may also be pulled away from the distal end of the catheter body 256 during or after the balloon 254 is being deflated to minimize the profile of the balloon and scoring structure. Alternatively, the manipulator 360 may be used to rotate the attachment structure 258 with respect to the catheter body 256 to control the compliance of the balloon and scoring structure during transition from a collapsed to expanded state and back to a collapsed state.

Figure 21:
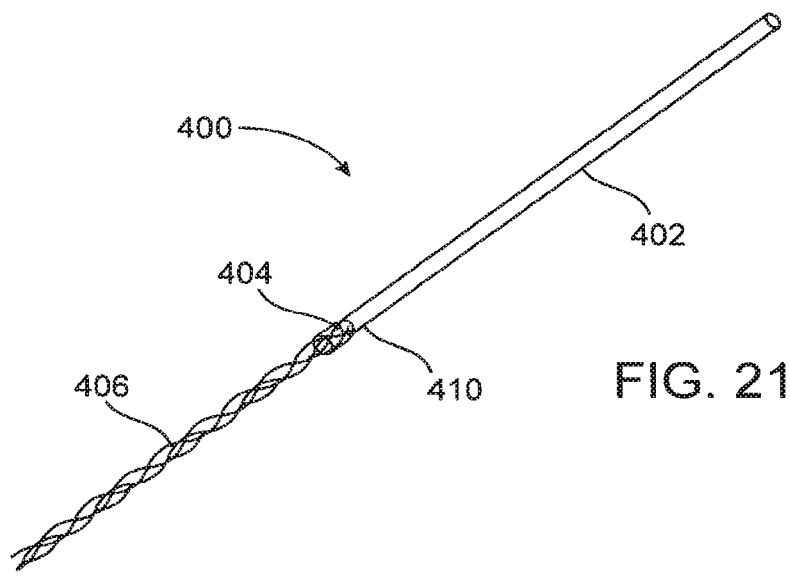
FIG. 21 illustrates an embodiment of the invention having a laminated section at the distal end of the compliance tube.
Figure 22:
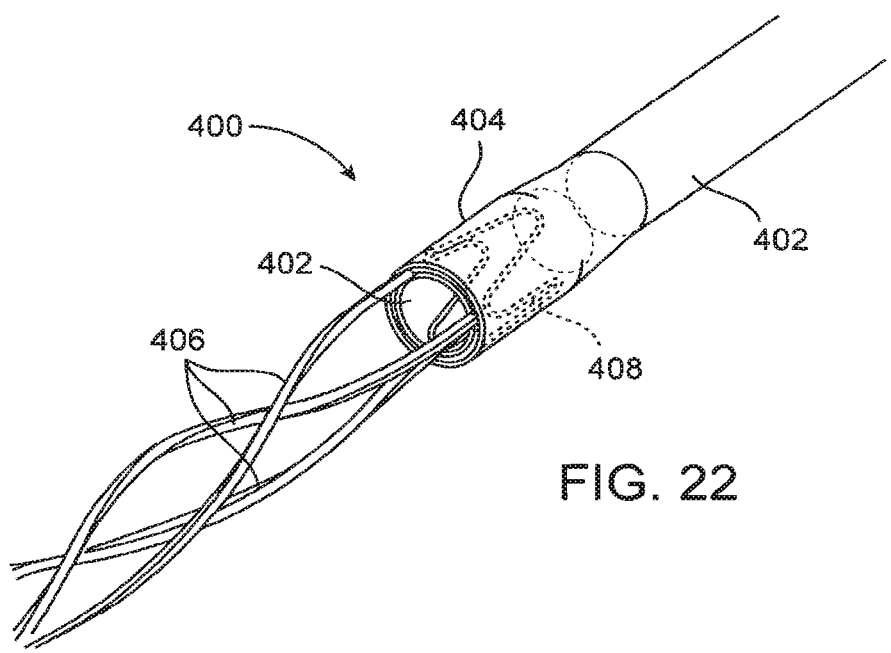
FIG. 22 illustrates another view of the embodiment of FIG. 21.

Now referring to FIGS. 21 and 22, a scoring cage structure 400 is illustrated having a two-layer laminated compliance tube 402. As shown in FIG. 22, the compliance tube 402 has a laminated structure 404 at least its distal end 410. The laminated structure holds the proximal ends 408 of the scoring elements 406 as shown in broken line in FIG. 22. The scoring elements 406 may be sized to fit over the outside of the compliance tube 402, as illustrated in FIG. 22, with the lamination covering the elements. Alternatively, the compliance sleeve tube 402 may be sized to fit inside of the scoring structure 406, with the laminating layer(s) formed over the elements 406 (not shown).

The laminating structure may be composed of a polymer similar to the compliance tube 402, and may be heat shrunk or melted to thermally bond the compliance sleeve to the compliance tube and sandwich the scoring structure 406. Alternatively, an adhesive or other bonding method such as ultrasonic or RF energy may be used to laminate the structure. The laminated structure as shown in FIGS. 21 and 22, provides a smoothed transition and strengthened bond between the scoring cage and the attachment structure. Such a smooth transition is a particular advantage when withdrawing the scoring cage from the vasculature.

Figure 23:
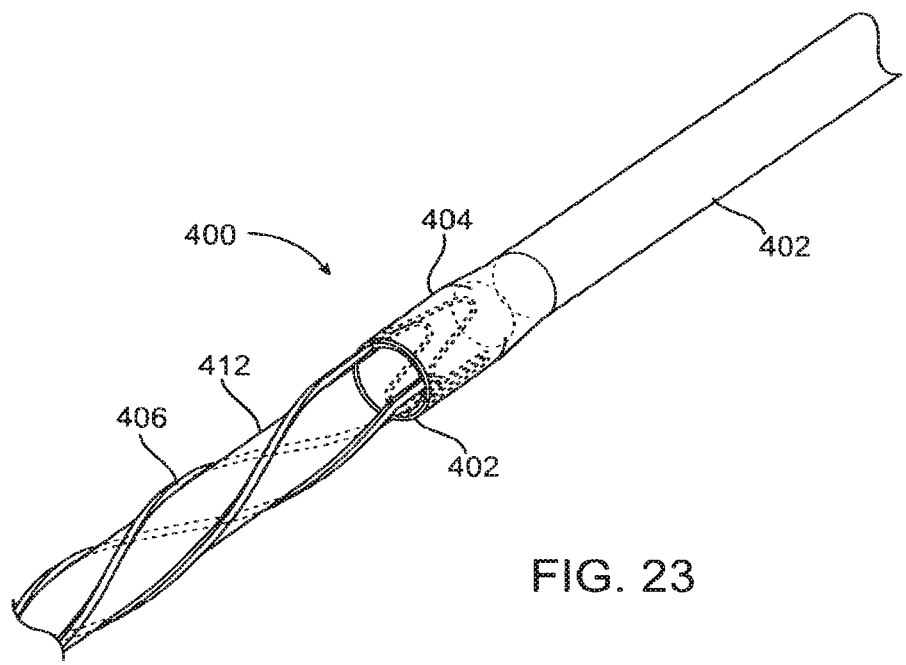
FIG. 23 illustrates the embodiment of FIG. 21 with an expandable balloon inserted within the scoring structure.
Figure 24:
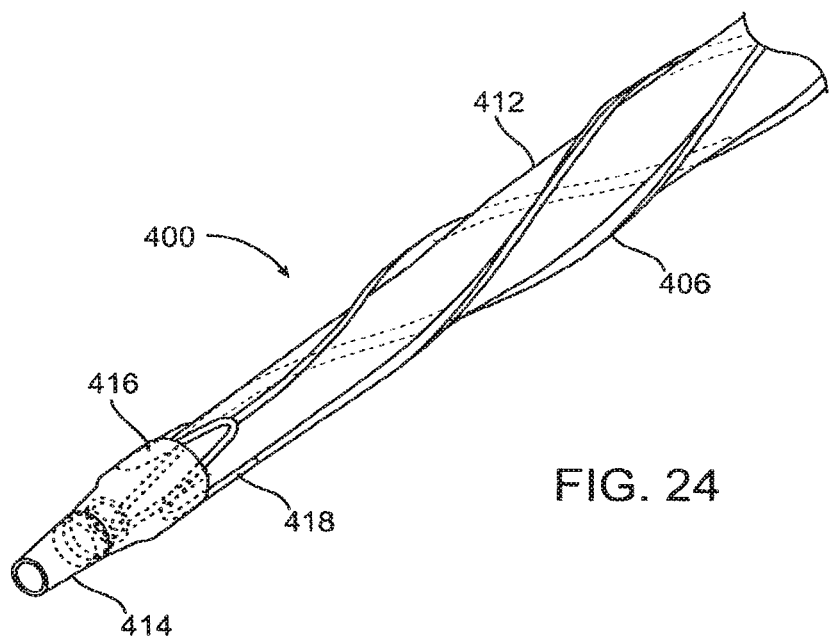
FIG. 24 illustrates an embodiment with a sleeve over the distal end of the scoring structure.

FIGS. 23 and 24 illustrate scoring cage 400 positioned over an expandable dilation balloon 412. As shown in FIG. 24, distal end 418, of the scoring structure may be coupled to the distal tip 414 of the catheter body by an end cap 416. The end cap 416 may be composed of a compatible polymer and thermally bonded with the catheter body to fax distal end 418 of the scoring structure to the catheter body.

Figure 25:
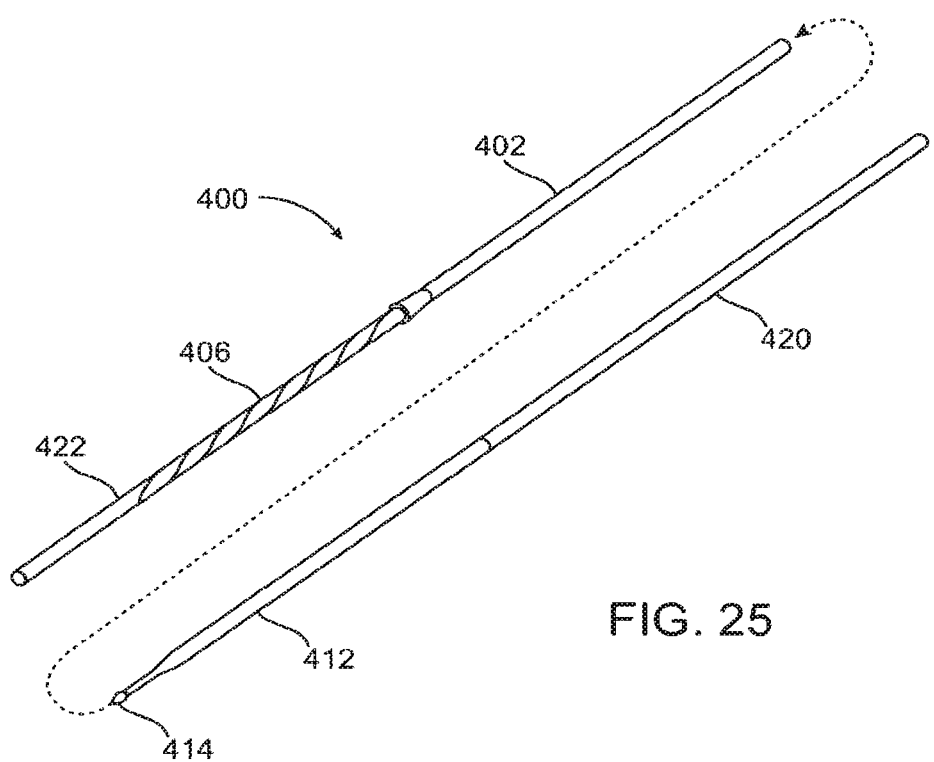
FIG. 25 illustrates a method of the present invention utilizing an insertion tube to mount the scoring structure over the expandable balloon.
Figure 26:
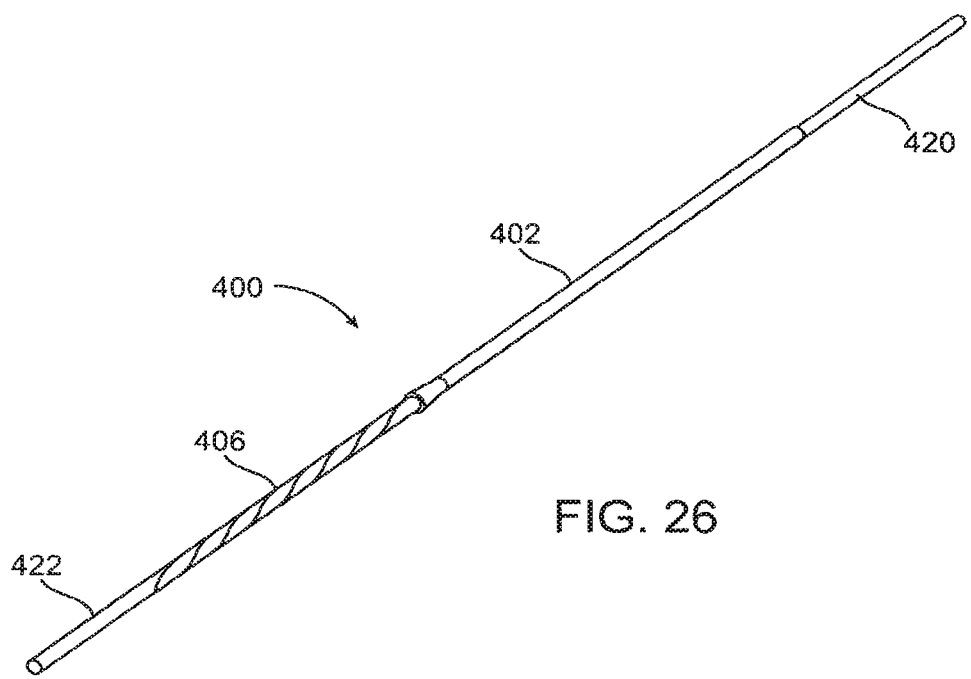
FIG. 26 illustrates shows the insertion tube inserted over the expandable balloon.
Figure 27:
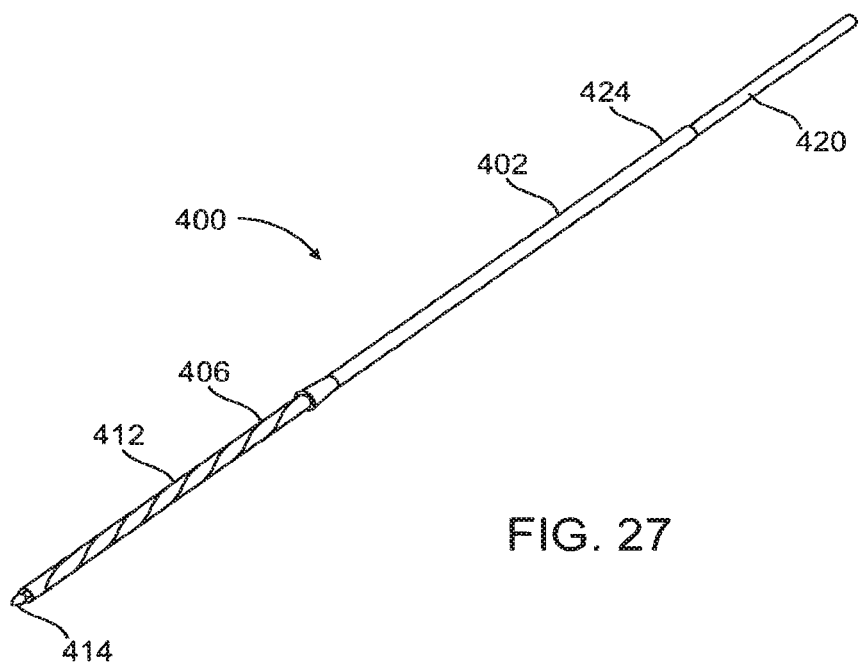
FIG. 27 illustrates a scoring catheter of the present invention with the insertion tube removed.

Now referring to FIGS. 25-27, a method is illustrated for mounting an expandable scoring cage 406 over a balloon catheter. The scoring cage 406 is pre-expanded by loading it over an insertion tube 422 that has an inner diameter slightly larger than the outer diameter of the balloon 412. A catheter body 420 having a balloon 412 is then inserted into the inner diameter of the insertion tube 422 and advanced until the balloon 412 is appropriately positioned with respect to the scoring structure 406, as illustrated in FIG. 26. The insertion tube 422 is then pulled back to allow the expanded scoring structure to collapse over the balloon 412 and the catheter body 420, as shown in FIG. 27. The scoring structure 406 may then be secured at its distal end 418 to the distal tip 414 of the catheter body 420 and the proximal end 424 of the scoring structure/attachment structure assembly to a medial location on the catheter body 420.

As described thus far, the scoring structures and catheter apparatus have not included any drugs, active substances, or other coatings or features related to releasing such drugs or substances into the vasculature or other body lumens. The scoring elements, however, can be easily modified by a variety of known techniques for incorporating such drugs and active substances on, over, or within the structures of the scoring elements, as illustrated for example in FIGS. 28-34. The drugs and other active substances can be applied to one or more surface regions of the scoring elements by conventional techniques, such as dipping, painting, vapor deposition, spin coating, and the like. The active substances may be applied in an essentially pure form, i.e., in the absence of any carriers, diluents, adjuvants, modifiers, enhancers, or the like. More commonly, however, the active substances will be applied with or combined into a suitable carrier, matrix, or other chemical structure which can facilitate or control release of the drug over a desired time period or immediately upon expansion of the scoring element or shortly after being introduce to the body lumen. In particular examples, a resorbable or non-resorbable polymer matrix may first be applied on at least a portion of an exposed surface of the scoring element, and the drug later absorbed into a porous structure of the polymer carrier matrix. Suitable materials for both resorbable and non-resorbable polymers have been described above.

Figure 28:
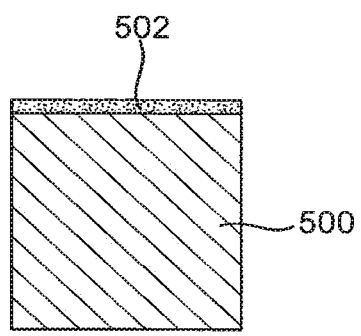
FIGS. 28-34 illustrate different configurations for coating or otherwise coupling an active substance on or within a scoring element in accordance with the principles of the present invention.
Figure 29:
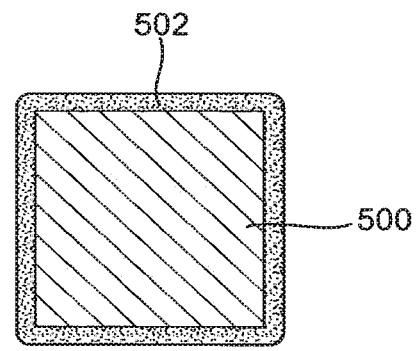

Referring to FIGS. 28 and 29, a scoring element or strut 500 can be coated with a pure or substantially pure layer 502 of a desired active substance. As shown in FIG. 28, the active substance layer 502 can be confined to a limited surface or surfaces of the scoring element 500. Alternatively, as shown in FIG. 29, the active substance layer 502 can cover all or most of the exposed surfaces of the scoring element 500.

Figure 30:
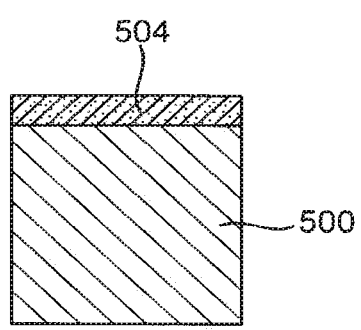
Figure 31:
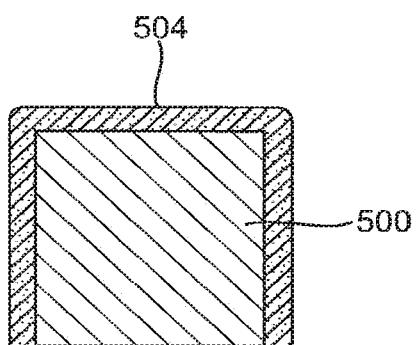

Referring now to FIGS. 30 and 31, scoring element 500 may be covered with a polymer matrix 504 which can cover a limited surface or surfaces of the element (as shown in FIG. 30), or all or most of the surfaces (as shown in FIG. 31). The active substance will be absorbed into porous regions of the polymer matrix 504 by conventional techniques. Resorbable polymers, such as polylactic acids and polyglycolic acids, will degrade and be resorbed over time when exposed to a vascular environment. In such cases, release of the active substance from the matrix may be effected by either the degradation where the drug is released as the polymer decomposes or by combination of degradation and diffusion through the porous structure. In the case of non-resorbable polymers, the active substance will typically be released by a diffusion mechanism and the polymer will remain for sometime after diffusion has substantially stopped (although the polymer could degrade over a longer time period). In other examples, the polymer (e.g. poly ethylene oxide) can swell and the diffusion may be enhanced by the swelling process.

Figure 32:
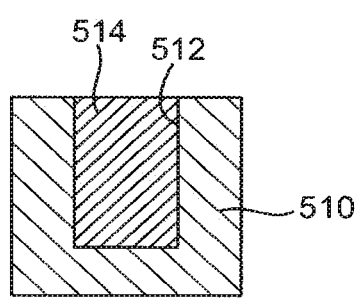

Referring now to FIG. 32, scoring element 510 may be modified to have a well 512, typically a plurality of wells, at least some of which will hold a polymer matrix 514. The polymer matrix may be degradable or nondegradable, as described above, and will release an incorporated active substance by either of the mechanisms described.

Figure 33:
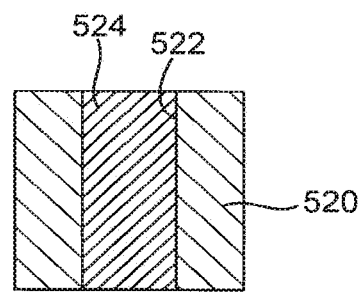

As shown if FIG. 33, scoring element 520 may comprise one or more holes 522, some or all of which contain a polymer matrix 524. The hole 522 differs from the well 512 (FIG. 32) in that no bottom structure is provided and the well is opened at each end. The active substance may be incorporated in the polymer matrix and released by any of the mechanisms described above.

It will be appreciated that with either the well 512 or the hole 522, the polymer matrix may be composed of layers having different properties and/or include layers composed of different polymers or other materials. In this way, a variety of release mechanisms can be achieved.

Figure 34:
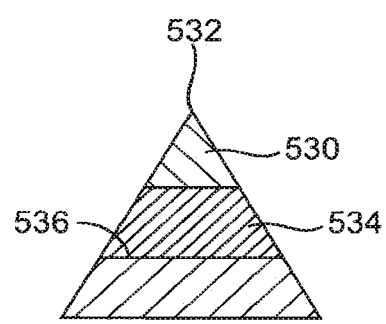

Referring now to FIG. 34, a scoring element 530 having a sharpened or honed ridge 532 can also be provided with an active substance. As shown in FIG. 34, the active substance is incorporated in a polymer matrix 534 which is disposed a horizontal through hole 536, The through hole is composed of a resorbable or non-resorbable polymer and the active substance is incorporated therein and released by the mechanisms described above. It will be appreciated, however, that the triangular elements, or any other scoring elements could also be coated with a drug directly or incorporated in a polymer matrix which is disposed over exterior surface(s) of the element. Additionally, it would be possible to further coat the scoring element 530 of FIG. 34 with drug over all or a portion of its exterior surface(s) while also including the internally sequestered drug in the through hole 536.

Figure 35:
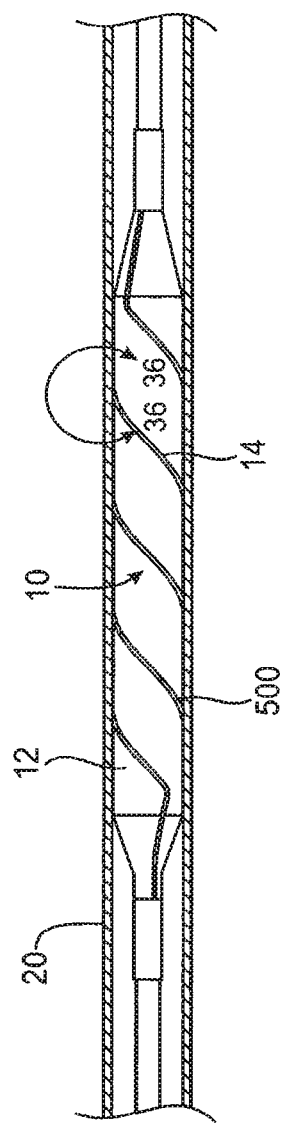
FIGS. 35, 36A, and 36B illustrate use of the scoring elements of the present invention for delivering an active substance to a wall site in a blood vessel.
Figure 36B:
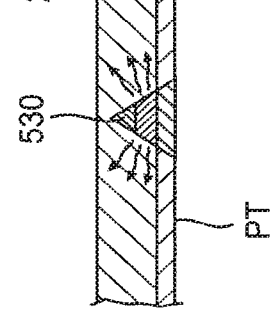
Figure 36A:
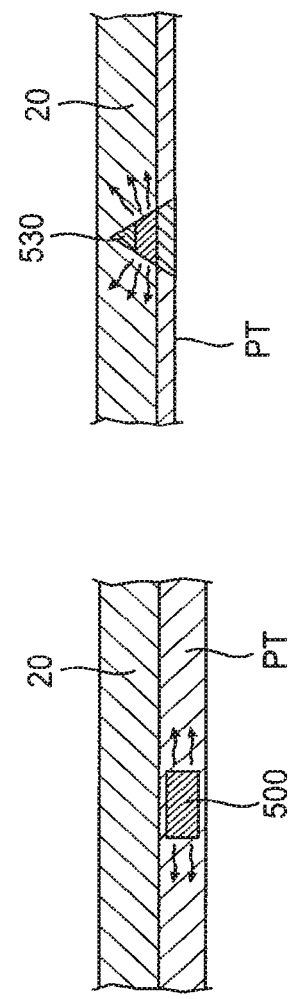

Referring now to FIGS. 35, 36A, and 36B, use of the scoring element structures of the present invention for delivering an active substance to a blood vessel will be described. Balloon 12 of dilatation device 10 is expanded within a diseased region of a blood vessel 20, as generally described above. Scoring elements 500 of the dilatation device have incorporated drug, typically an anti-proliferative drug of the type described above, incorporated in or over their surfaces and structures, by any of the means described above. As shown in FIG. 36A, in an exemplary embodiment, the scoring element 500 may penetrate into hardened plaque or thrombus PT as the balloon 12 is expanded. The scoring element will penetrate into the plaque or thrombus PT and release drug, possibly a thrombolytic drug, into the plaque and thrombus. In other cases, a scoring element, such as the honed scoring element 530 might be expanded by balloon 12 so that it enters into the blood vessel wall 20, as illustrated in FIG. 36B. In those cases, the drug may be released directly into the intimal or other regions of the blood vessel wall.

It will be appreciated by persons skilled in the art that the present invention is not limited to what has been particularly shown and described hereinabove. Alternate embodiments are contemplated that fall within the scope of the invention.

What is claimed is:

1. A catheter for delivering an active substance to a luminal site, the catheter comprising:
   a catheter body having a proximal portion and a distal portion;
   an expandable shell coupled to the distal portion of the catheter body;
   a scoring structure comprising at least one scoring element disposed over the expandable shell, wherein the scoring element comprises a proximal end and a distal end, wherein one of the proximal end of the scoring element or the distal end of the scoring element is stationary relative to the catheter body and the other of the proximal end and the distal end of the scoring element is axially moveable relative to the catheter body; and an active substance carried by the at least one scoring element;

whereupon positioning the at least one scoring element at the luminal site and expanding the expandable shell, the active substance is released from the at least one scoring element and delivered to the luminal site.

2. The catheter of claim 1, wherein the distal end of the scoring element is stationary relative to the catheter body and the proximal end of the scoring element is axially moveable relative to the catheter body.

3. The catheter of claim 1, wherein the at least one scoring element radially expands upon expanding the expandable shell.

4. The catheter of claim 1, wherein the at least one scoring element is elongate.

5. The catheter of claim 1, wherein the at least one scoring element has a helical geometry.

6. The catheter of claim 1, wherein the at least one scoring element has a rectangular cross-section.

7. The catheter of claim 1, wherein the at least one scoring element has a triangular cross-section.

8. The catheter of claim 7, wherein the triangular cross-section of the at least one scoring element comprises a sharpened or honed ridge.

9. The catheter of claim 1, wherein the scoring structure comprises a plurality of scoring elements.

10. The catheter of claim 1, wherein the expandable shell comprises a balloon.

11. The catheter of claim 1, wherein the active substance comprises one or more of an antiproliferative agent, an antimitotic agent, an antiplatelet agent, an alkylating agent, an antimetabolite, a platinum coordination complex, a hormone, an anticoagulant, a fibrinolytic agent, an antimigratory agent, an antisecretory agent, an anti-inflammatory agent, indole and acetic acids, an immunosuppressive agent, an angiogenic agent, an angiotensin receptor blocker, a nitric oxide donor, an anti-sense oligonucleotide, a cell cycle inhibitor, a retinoid, a cyclin/CDK inhibitor, an HMG co-enzyme reductase inhibitor, and a protease inhibitor.

12. The catheter of claim 1, wherein the active substance comprises an antiproliferative drug.

13. The catheter of claim 1, wherein the active substance comprises paclitaxel.

14. The catheter of claim 1, wherein at least a portion of an exposed surface of the at least one scoring element comprises a coating having the active substance.

15. The catheter of claim 14, wherein the coating comprises a polymeric carrier and the active substance is incorporated in the polymeric carrier.

16. The catheter of claim 1, wherein at least one scoring element comprises one or more wells and the active substance is carried in the one or more wells.

17. The catheter of claim 16, wherein the active substance is incorporated in a polymeric carrier and the polymeric carrier is carried in the one or more wells.

18. The catheter of claim 1, wherein at least one scoring element comprises one or more holes and the active substance is carried in the one or more holes.

19. The catheter of claim 18, wherein the active substance is incorporated in a polymeric carrier and the polymeric carrier is carried in the one or more holes.

* * * * *